(12) United States Patent
Libbus et al.

(10) Patent No.: US 10,500,398 B2
(45) Date of Patent: Dec. 10, 2019

(54) NEUROSTIMULATION TITRATION PROCESS VIA ADAPTIVE PARAMETRIC MODIFICATION

(71) Applicant: LivaNova USA, Inc., Houston, TX (US)

(72) Inventors: Imad Libbus, St. Paul, MN (US); Bruce H. KenKnight, Maple Grove, MN (US); Badri Amurthur, Los Gatos, CA (US); Scott R. Stubbs, Maple Grove, MN (US)

(73) Assignee: LivaNova USA, Inc., Houston, TX (US)

( * ) Notice: Subject to any disclaimer, the term of this patent is extended or adjusted under 35 U.S.C. 154(b) by 197 days.

(21) Appl. No.: 15/360,188

(22) Filed: Nov. 23, 2016

(65) Prior Publication Data

US 2017/0106192 A1  Apr. 20, 2017

Related U.S. Application Data

(63) Continuation of application No. 14/563,181, filed on Dec. 8, 2014, now Pat. No. 9,504,832.
(Continued)

(51) Int. Cl.
*A61N 1/36* (2006.01)
*A61N 1/05* (2006.01)
(Continued)

(52) U.S. Cl.
CPC ........ *A61N 1/36139* (2013.01); *A61B 5/0452* (2013.01); *A61N 1/0551* (2013.01); *A61N 1/3615* (2013.01); *A61N 1/36114* (2013.01); *A61N 1/36132* (2013.01); *A61N 1/36167* (2013.01); *A61N 1/3702* (2013.01); *A61N 1/37223* (2013.01); *A61N 1/37235* (2013.01); *G06F 19/00* (2013.01); *G06F 19/325* (2013.01); *G16H 20/40* (2018.01); *G16H 40/63* (2018.01); *G16Z 99/00* (2019.02)

(58) Field of Classification Search
CPC ............ A61N 1/36167; A61N 1/36114; A61N 1/36132; A61N 1/3615; A61N 1/37223; A61N 1/37235
See application file for complete search history.

(56) References Cited

U.S. PATENT DOCUMENTS 5,330,507 A   7/1994  Schwartz
5,522,854 A   6/1996  Ideker et al.
(Continued)

OTHER PUBLICATIONS

US 8,315,702 B2, 11/2012, Chavan et al. (withdrawn)
(Continued)

*Primary Examiner* — Amanda K Hulbert
(74) *Attorney, Agent, or Firm* — Foley & Lardner LLP

(57) ABSTRACT

Systems and methods are provided for delivering neurostimulation therapies to patients. A titration process is used to gradually increase the stimulation intensity to a desired therapeutic level. Between titration sessions one or more parameters, such as, for example, an acclimation interval, may be adjusted based on the patient's response to the stimulation. This personalized titration process can minimize the amount of time required to complete titration so as to begin delivery of the stimulation at therapeutically desirable levels.

20 Claims, 13 Drawing Sheets

Related U.S. Application Data

(60) Provisional application No. 62/078,600, filed on Nov. 12, 2014.

(51) Int. Cl.
    *G16H 40/63*     (2018.01)
    *A61N 1/372*     (2006.01)
    *A61B 5/0452*    (2006.01)
    *A61N 1/37*      (2006.01)
    *G06F 19/00*     (2018.01)
    *G16H 20/40*     (2018.01)
    *G16Z 99/00*     (2019.01)

(56) References Cited

U.S. PATENT DOCUMENTS

| | | |
|---|---|---|
| 5,707,400 A | 1/1998 | Terry, Jr. et al. |
| 5,928,272 A | 7/1999 | Adkins et al. |
| 5,978,709 A | 11/1999 | Begemann et al. |
| 6,006,134 A | 12/1999 | Hill et al. |
| 6,266,564 B1 | 7/2001 | Hill et al. |
| 6,354,991 B1 | 3/2002 | Gross et al. |
| 6,449,507 B1 | 9/2002 | Hill et al. |
| 6,473,644 B1 | 10/2002 | Terry et al. |
| 6,508,771 B1 | 1/2003 | Padmanabhan et al. |
| 6,522,926 B1 | 2/2003 | Kieval et al. |
| 6,600,954 B2 | 7/2003 | Cohen et al. |
| 6,610,713 B2 | 8/2003 | Tracey |
| 6,616,624 B1 | 9/2003 | Kieval |
| 6,622,041 B2 | 9/2003 | Terry, Jr. et al. |
| 6,652,449 B1 | 11/2003 | Gross et al. |
| 6,684,105 B2 | 1/2004 | Cohen et al. |
| 6,690,971 B2 | 2/2004 | Schauerte et al. |
| 6,712,772 B2 | 3/2004 | Cohen et al. |
| 6,718,208 B2 | 4/2004 | Hill et al. |
| 6,838,471 B2 | 1/2005 | Tracey |
| 6,839,594 B2 | 1/2005 | Cohen et al. |
| 6,850,801 B2 | 2/2005 | Kieval et al. |
| 6,862,480 B2 | 3/2005 | Cohen et al. |
| 6,892,098 B2 | 5/2005 | Ayal et al. |
| 6,896,651 B2 | 5/2005 | Gross et al. |
| 6,904,318 B2 | 6/2005 | Hill et al. |
| 6,907,295 B2 | 7/2005 | Gross et al. |
| 6,963,773 B2 | 11/2005 | Waltman et al. |
| 6,963,779 B1 | 11/2005 | Shankar |
| 6,985,774 B2 | 1/2006 | Kieval et al. |
| 7,010,345 B2 | 3/2006 | Hill et al. |
| 7,072,720 B2 | 7/2006 | Puskas |
| 7,123,961 B1 | 10/2006 | Kroll et al. |
| 7,136,705 B1 | 11/2006 | Park |
| 7,139,607 B1 | 11/2006 | Shelchuk |
| 7,158,832 B2 | 1/2007 | Kieval et al. |
| 7,184,828 B2 | 2/2007 | Hill et al. |
| 7,184,829 B2 | 2/2007 | Hill et al. |
| 7,189,204 B2 | 3/2007 | Ni et al. |
| 7,218,964 B2 | 5/2007 | Hill et al. |
| 7,221,979 B2 | 5/2007 | Zhou et al. |
| 7,225,017 B1 | 5/2007 | Shelchuk |
| 7,225,019 B2 | 5/2007 | Jahns et al. |
| 7,237,320 B2 | 7/2007 | Lam |
| 7,245,967 B1 | 7/2007 | Shelchuk |
| 7,260,431 B2 | 8/2007 | Libbus et al. |
| 7,269,457 B2 | 9/2007 | Shafer et al. |
| 7,277,761 B2 | 10/2007 | Shelchuk |
| 7,295,881 B2 | 11/2007 | Cohen et al. |
| 7,305,265 B2 | 12/2007 | Fukui |
| 7,321,793 B2 | 1/2008 | Ezra et al. |
| 7,324,853 B2 | 1/2008 | Ayal et al. |
| 7,336,997 B2 | 2/2008 | Fukui |
| 7,346,398 B2 | 3/2008 | Gross et al. |
| 7,387,603 B2 | 6/2008 | Gross et al. |
| 7,389,149 B2 | 6/2008 | Rossing et al. |
| 7,395,119 B2 | 7/2008 | Hagen et al. |
| 7,403,819 B1 | 7/2008 | Shelchuk et al. |
| 7,418,292 B2 | 8/2008 | Shafer |
| 7,452,800 B2 | 11/2008 | Sosnowchik et al. |
| 7,480,532 B2 | 1/2009 | Kieval et al. |
| 7,481,759 B2 | 1/2009 | Whitehurst et al. |
| 7,485,104 B2 | 2/2009 | Kieval |
| 7,493,167 B2 | 2/2009 | Hussein et al. |
| 7,499,742 B2 | 3/2009 | Bolea et al. |
| 7,499,747 B2 | 3/2009 | Kieval et al. |
| 7,499,748 B2 | 3/2009 | Moffitt et al. |
| 7,502,650 B2 | 3/2009 | Kieval |
| 7,542,800 B2 | 6/2009 | Libbus et al. |
| 7,548,780 B2 | 6/2009 | Libbus et al. |
| 7,551,958 B2 | 6/2009 | Libbus et al. |
| 7,561,922 B2 | 7/2009 | Cohen et al. |
| 7,561,923 B2 | 7/2009 | Libbus et al. |
| 7,570,999 B2 | 8/2009 | Libbus et al. |
| 7,582,053 B2 | 9/2009 | Gross et al. |
| 7,584,004 B2 | 9/2009 | Caparso et al. |
| 7,587,238 B2 | 9/2009 | Moffitt et al. |
| 7,606,622 B2 | 10/2009 | Reeve |
| 7,613,511 B2 | 11/2009 | Wu et al. |
| 7,613,516 B2 | 11/2009 | Cohen et al. |
| 7,616,990 B2 | 11/2009 | Chavan et al. |
| 7,617,003 B2 | 11/2009 | Caparso et al. |
| 7,623,926 B2 | 11/2009 | Rossing et al. |
| 7,627,384 B2 | 12/2009 | Ayal et al. |
| 7,628,750 B2 | 12/2009 | Cohen et al. |
| 7,630,760 B2 | 12/2009 | Libbus et al. |
| 7,634,315 B2 | 12/2009 | Cholette |
| 7,634,317 B2 | 12/2009 | Ben-David et al. |
| 7,640,057 B2 | 12/2009 | Libbus et al. |
| 7,647,101 B2 | 1/2010 | Libbus et al. |
| 7,647,114 B2 | 1/2010 | Libbus |
| 7,650,190 B2 | 1/2010 | Zhou et al. |
| 7,657,312 B2 | 2/2010 | Pastore et al. |
| 7,660,628 B2 | 2/2010 | Libbus et al. |
| 7,664,548 B2 | 2/2010 | Amurthur et al. |
| 7,668,602 B2 | 2/2010 | Ben-David et al. |
| 7,672,733 B2 | 3/2010 | Zhou et al. |
| 7,676,275 B1 | 3/2010 | Farazi et al. |
| 7,684,866 B2 | 3/2010 | Fowler et al. |
| 7,689,286 B2 | 3/2010 | Pastore et al. |
| 7,711,415 B1 | 5/2010 | Farazi et al. |
| 7,711,421 B2 | 5/2010 | Shafer et al. |
| 7,734,355 B2 | 6/2010 | Cohen et al. |
| 7,738,956 B1 | 6/2010 | Farazi et al. |
| 7,751,884 B2 | 7/2010 | Ternes et al. |
| 7,769,442 B2 | 8/2010 | Shafer |
| 7,769,446 B2 | 8/2010 | Moffitt et al. |
| 7,778,702 B2 | 8/2010 | Ben-David et al. |
| 7,778,703 B2 | 8/2010 | Gross et al. |
| 7,778,711 B2 | 8/2010 | Ben-David et al. |
| 7,783,353 B2 | 8/2010 | Libbus et al. |
| 7,797,041 B2 | 9/2010 | Libbus et al. |
| 7,801,603 B2 | 9/2010 | Westlund et al. |
| 7,801,604 B2 | 9/2010 | Brockway et al. |
| 7,801,614 B2 | 9/2010 | Rossing et al. |
| 7,805,193 B2 | 9/2010 | Libbus et al. |
| 7,805,203 B2 | 9/2010 | Ben-David et al. |
| 7,813,805 B1 | 10/2010 | Farazi |
| 7,813,812 B2 | 10/2010 | Kieval et al. |
| 7,835,797 B2 | 11/2010 | Rossing et al. |
| 7,840,266 B2 | 11/2010 | Libbus et al. |
| 7,840,271 B2 | 11/2010 | Kieval et al. |
| 7,844,346 B2 | 11/2010 | Cohen et al. |
| 7,848,812 B2 | 12/2010 | Crowley et al. |
| 7,848,816 B1 | 12/2010 | Wenzel et al. |
| 7,869,869 B1 | 1/2011 | Farazi |
| 7,885,709 B2 | 2/2011 | Ben-David |
| 7,885,711 B2 | 2/2011 | Ben-Ezra et al. |
| 7,890,185 B2 | 2/2011 | Cohen et al. |
| 7,894,907 B2 | 2/2011 | Cowan et al. |
| 7,904,151 B2 | 3/2011 | Ben-David et al. |
| 7,904,175 B2 | 3/2011 | Scott et al. |
| 7,904,176 B2 | 3/2011 | Ben-Ezra et al. |
| 7,908,008 B2 | 3/2011 | Ben-David et al. |
| 7,916,013 B2 | 3/2011 | Stevenson |
| 7,925,342 B2 | 4/2011 | Amurthur et al. |
| 7,925,352 B2 | 4/2011 | Stack et al. |
| 7,974,693 B2 | 7/2011 | Ben-David et al. |

(56) References Cited

U.S. PATENT DOCUMENTS

| | | |
|---|---|---|
| 7,991,456 B2 | 8/2011 | Chow |
| 8,005,542 B2 | 8/2011 | Ben-Ezra et al. |
| 8,005,545 B2 | 8/2011 | Ben-David et al. |
| 8,036,745 B2 | 10/2011 | Ben-David et al. |
| 8,060,197 B2 | 11/2011 | Ben-David et al. |
| 8,065,021 B2 | 11/2011 | Gross et al. |
| 8,083,663 B2 | 12/2011 | Gross et al. |
| 8,116,881 B2 | 2/2012 | Cohen et al. |
| 8,131,362 B2 | 3/2012 | Moffitt et al. |
| 8,160,701 B2 | 4/2012 | Zhao et al. |
| 8,160,705 B2 | 4/2012 | Stevenson et al. |
| 8,195,290 B2 | 6/2012 | Brockway et al. |
| 8,224,436 B2 | 7/2012 | Libbus et al. |
| 8,249,711 B2 | 8/2012 | Libbus et al. |
| 8,369,943 B2 | 2/2013 | Shuros et al. |
| 8,386,038 B2 | 2/2013 | Bianchi et al. |
| 8,401,640 B2 | 3/2013 | Zhao et al. |
| 8,417,354 B2 | 4/2013 | Zhang et al. |
| 8,437,837 B2 | 5/2013 | Zhou |
| 8,571,654 B2 | 10/2013 | Libbus et al. |
| 8,577,458 B1 | 11/2013 | Libbus et al. |
| 8,600,505 B2 | 12/2013 | Libbus et al. |
| 8,634,921 B2 | 1/2014 | Chavan et al. |
| 8,688,212 B2 | 4/2014 | Libbus et al. |
| 8,918,190 B2 | 12/2014 | Libbus et al. |
| 2002/0107553 A1 | 8/2002 | Hill et al. |
| 2003/0040774 A1 | 2/2003 | Terry et al. |
| 2003/0153954 A1 | 8/2003 | Park et al. |
| 2003/0171781 A1 | 9/2003 | Florio et al. |
| 2004/0199210 A1 | 10/2004 | Shelchuk |
| 2004/0210261 A1 | 10/2004 | King et al. |
| 2004/0215265 A1 | 10/2004 | Keizer |
| 2005/0049655 A1 | 3/2005 | Boveja et al. |
| 2005/0065553 A1 | 3/2005 | Ezra et al. |
| 2005/0125044 A1 | 6/2005 | Tracey |
| 2005/0131467 A1 | 6/2005 | Boveja |
| 2005/0165465 A1 | 7/2005 | Pianca et al. |
| 2005/0267542 A1 | 12/2005 | David et al. |
| 2006/0015153 A1 | 1/2006 | Gliner et al. |
| 2006/0100668 A1 | 5/2006 | Ben-David et al. |
| 2006/0116592 A1 | 6/2006 | Zhou et al. |
| 2006/0190053 A1 | 8/2006 | Dobak, III |
| 2006/0206155 A1 | 9/2006 | Ben-David et al. |
| 2006/0253161 A1 | 11/2006 | Libbus et al. |
| 2007/0067004 A1* | 3/2007 | Boveja ............... A61N 1/36017 607/45 |
| 2007/0093870 A1 | 4/2007 | Maschino |
| 2007/0213773 A1 | 9/2007 | Hill et al. |
| 2007/0233194 A1 | 10/2007 | Craig |
| 2007/0239210 A1 | 10/2007 | Libbus et al. |
| 2007/0255320 A1 | 11/2007 | Inman et al. |
| 2007/0276453 A1 | 11/2007 | Hill et al. |
| 2008/0015659 A1 | 1/2008 | Zhang et al. |
| 2008/0021503 A1 | 1/2008 | Whitehurst et al. |
| 2008/0033511 A1 | 2/2008 | Dobak |
| 2008/0051839 A1 | 2/2008 | Libbus et al. |
| 2008/0058874 A1 | 3/2008 | Westlund et al. |
| 2008/0061240 A1 | 3/2008 | Heuft |
| 2008/0082133 A1 | 4/2008 | Zhou |
| 2008/0091240 A1 | 4/2008 | Ben-David et al. |
| 2008/0132983 A1 | 6/2008 | Cohen et al. |
| 2008/0135864 A1 | 6/2008 | David et al. |
| 2008/0147140 A1 | 6/2008 | Ternes et al. |
| 2008/0183258 A1 | 7/2008 | Inman |
| 2008/0243196 A1 | 10/2008 | Libbus et al. |
| 2008/0319513 A1 | 12/2008 | Pu et al. |
| 2009/0024186 A1 | 1/2009 | Brockway et al. |
| 2009/0030493 A1 | 1/2009 | Colborn et al. |
| 2009/0118777 A1 | 5/2009 | Iki et al. |
| 2009/0124848 A1 | 5/2009 | Miazga |
| 2009/0149900 A1 | 6/2009 | Moffitt et al. |
| 2009/0248097 A1 | 10/2009 | Tracey et al. |
| 2009/0270953 A1 | 10/2009 | Ecker et al. |
| 2009/0275956 A1 | 11/2009 | Burnes et al. |
| 2009/0326595 A1 | 12/2009 | Brockway et al. |
| 2010/0010556 A1 | 1/2010 | Zhao et al. |
| 2010/0010603 A1 | 1/2010 | Ben-David et al. |
| 2010/0016919 A1 | 1/2010 | Hill et al. |
| 2010/0042173 A1 | 2/2010 | Farazi et al. |
| 2010/0113954 A1 | 5/2010 | Zhou |
| 2010/0114197 A1 | 5/2010 | Burnes et al. |
| 2010/0114203 A1 | 5/2010 | Burnes et al. |
| 2010/0114227 A1 | 5/2010 | Cholette et al. |
| 2010/0174341 A1 | 7/2010 | Bolea et al. |
| 2010/0286740 A1 | 11/2010 | Libbus et al. |
| 2010/0331908 A1 | 12/2010 | Farazi |
| 2011/0015692 A1 | 1/2011 | Libbus et al. |
| 2011/0082514 A1 | 4/2011 | Libbus et al. |
| 2011/0098796 A1 | 4/2011 | Ben-David et al. |
| 2011/0224749 A1 | 9/2011 | Ben-David et al. |
| 2011/0257708 A1 | 10/2011 | Kramer et al. |
| 2011/0270332 A1 | 11/2011 | Buschman et al. |
| 2011/0301479 A1 | 12/2011 | Ghanem et al. |
| 2011/0313488 A1 | 12/2011 | Hincapie Ordonez et al. |
| 2012/0143286 A1* | 6/2012 | Hahn ............... A61N 1/36132 607/59 |
| 2012/0172742 A1 | 6/2012 | Arcot-Krishnamurthy et al. |
| 2012/0185007 A1 | 7/2012 | Ziegler et al. |
| 2012/0185010 A1 | 7/2012 | Zhou et al. |
| 2012/0192874 A1 | 8/2012 | Bolea et al. |
| 2012/0271374 A1 | 10/2012 | Nelson et al. |
| 2012/0303080 A1 | 11/2012 | Ben-David et al. |
| 2013/0158616 A1 | 6/2013 | Libbus et al. |
| 2013/0158617 A1 | 6/2013 | Libbus et al. |
| 2013/0158618 A1 | 6/2013 | Libbus et al. |
| 2013/0238047 A1 | 9/2013 | Libbus et al. |
| 2013/0289646 A1 | 10/2013 | Libbus et al. |
| 2014/0025132 A1 | 1/2014 | Libbus et al. |
| 2014/0135862 A1 | 5/2014 | Libbus et al. |
| 2014/0135863 A1 | 5/2014 | Libbus et al. |
| 2014/0135864 A1 | 5/2014 | Libbus et al. |
| 2014/0228905 A1 | 8/2014 | Bolea |
| 2014/0277232 A1 | 9/2014 | Libbus et al. |
| 2015/0073511 A1 | 3/2015 | Libbus et al. |
| 2015/0073512 A1 | 3/2015 | Libbus et al. |
| 2015/0094962 A1 | 4/2015 | Hoegh et al. |
| 2015/0119956 A1 | 4/2015 | Libbus et al. |
| 2015/0119959 A1 | 4/2015 | Libbus et al. |
| 2015/0196762 A1 | 7/2015 | Amurthur et al. |

OTHER PUBLICATIONS

Zhang, et al., "Chronic Vagus Nerve Stimulation Improves Autonomic Control and Attenuates Systemic Inflammation and Heart Failure Progression in a Canine High-Rate Pacing Model," Journal of the American Heart Association, Circ Heart Fail, 2, pp. 692-699 (2009).

Abraham, et al., "Devices in the management of advanced, chronic heart failure," Nature Reviews, vol. 10, pp. 98-110 (Feb. 2013) (Published online Dec. 11, 2012).

Adamson, et al., "Continuous Autonomic Assessment in Patients with Symptomatic Heart Failure: Prognostic Value of Heart Rate Variability Measured by an Implanted Cardiac Resynchronization Device," Circulation, Journal of the American Heart Association, 110, pp. 2389-2394 (2004).

Agostoni, et al., "Functional and Histological Studies of the Vagus Nerve and its Branches to the Heart, Lungs and Abdominal Viscera in the Cat," J. Physiol. 135, pp. 182-205 (1957).

Ajani, et al., "Prevalence of High C-Reactive Protein in Persons with Serum Lipid Concentrations within Recommended Values," Chemical Chemistry, 50:9, pp. 1618-1622 (2004).

Akiyama, et al., "Effects of right and left vagal stimulation on left ventricular acetylcholine levels in the cat," Acta Physiol Scand, 172, pp. 11-16 (2001).

Anand, et al., "C-Reactive Protein in Heart Failure: Prognostic Value and the Effect of Valsartan," Circulation, Journal of the American Heart Association, 112, pp. 1428-1434 (2005).

Anholt, et al., "Recruitment and blocking properties of the CardioFit stimulation lead," Journal of Neural Engineering, 8, pp. 1-6, (2011).

Ardell, et al.; "Selective vagal innervation of sinoatrial and atrioventricular nodes in canine heart," Am. J. Physiol. 251 (Heart Circ. Physiol. 20), pp. H764-H773 (1986).

(56) References Cited

OTHER PUBLICATIONS

Armour, "Cardiac neuronal hierarchy in health and disease," Am J Physiol Regul Integr Comp Physiol, 287, pp. R262-R271 (2004).
Armour, "Myocardial ischaemia and the cardiac nervous system," Cardiovascular Research, 41, pp. 41-54 (1999).
Armour, "The little brain on the heart," Cleveland Clinic Journal of Medicine, vol. 74, supp. 1, pp. S48-S51 (Feb. 2007).
Armour, et al., "Functional anatomy of canine cardiac nerves," Acta anat., 91, pp. 510-528 (1975).
Armour, et al., "Localized myocardial responses to stimulation of small cardiac branches of the vagus," American Journal of Physiology, vol. 228, No. 1 pp. 141-148 (Jan. 1975).
Armour, JA, "Potential clinical relevance of the 'little brain' on the mammalian heart," Experimental Physiology, vol. 1 93, No. 2, pp. 165-176 (Feb., 2008). Online Publication Date: Nov. 2, 2007. Available at: http://ep.physoc.org/content/93/2/165.long.
Asala, et al., "An electron microscope study of vagus nerve composition in the ferret," Anat Embryol, 175, pp. 247-253 (1986).
Aukrust, et al., "Inflammatory and anti-inflammatory cytokines in chronic heart failure: Potential therapeutic implications," Annals of Medicine, 37, pp. 74-85 (2005).
Author Unknown, "Nerve fiber—Types and Function," www.boddunan.com Available at www.boddunan.com/education/20-medicine-a-surgery/12730-nerver-fiber-types-and-function.html (Apr. 19, 2010).
Author Unknown, American Diabetes Association, "Standards of Medical Care in Diabetes—2012," Diabetes Care, vol. 35, supplement 1, pp. S11-S63 (Jan. 2012).
Author Unknown, Staff of Adinstruments, "Principles of Nerve Stimulation," Application Note, ADInstruments (Apr. 2002).
Bae, et al., "Gliosis in the Amygdala Following Myocardial Infarction in the Rat," J Vet Med Sci, 72(8), pp. 1041-1045 (2010).
Bernik, et al., "Pharmacological Stimulation of the Cholinergic Antiinflammatory Pathway," J. Exp. Med, vol. 195, No. 6, pp. 781-788 (Mar. 18, 2002).
Berthoud, et al., "Functional and chemical anatomy of the afferent vagal system," Autonomic Neuroscience: Basic and Clinical, 85, pp. 1-17 (2000).
Bhagat, et al., "Differential Effect of Right and Left Vagal Stimulation on Right and Left Circumflex Coronary Arteries," S A Medical Journal, 50, pp. 1591-1594 (1976).
Biasucci, et al., "Elevated Levels of C-Reactive Protein at Discharge in Patients with Unstable Angina Predict Recurrent Instability," Circulation, Journal of the American Heart Association, 99, pp. 855-860 (1999).
Bibevski, et al., "Evidence for impaired vagus nerve activity in heart failure," Heart Fail Rev, 16, pp. 129-135 (2011).
Bibevski, et al., "Ganglionic Mechanisms Contribute to Diminished Vagal Control in Heart Failure," Circulation, Journal of the American Heart Association, 99, pp. 2958-2963 (1999).
Bilgutay, et al., "Vagal Tuning A new concept in the treatment of supraventricular arrhythmias, angina pectoris, and heart failure," Journal of Thoracic and Cardiovascular Surgery, vol. 56, No. 1, pp. 71-82 (Jul. 1968).
Binkley, et al., "Parasympathetic Withdrawal is an Integral Component of Autonomic Imbalance in Congestive Heart Failure: Demonstration in Human Subjects and Verification in a Paced Canine Model of Ventricular Failure," JACC, vol. 18, No. 2, pp. 464-472 (Aug. 1991).
Bois, et al., "Mode of action of bradycardic agent, S 16257, on ionic currents of rabbit sinoatrial node cells," Abstract, British Journal of Pharmacology, 118(4):1051-7 (1996).
Bonaz, et al., "Vagus nerve stimulation: From epilepsy to the cholinergic anti-inflammatory pathway," Neurogastroenterology & Motility, pp. 1-14 (2013).
Borggrefe, et al., "Vagal Stimulation Devices," ESC Congress 2010 (2010).
Borovilkova, et al., "Vagus nerve stimulation attenuates the systemic inflammatory response to endotoxin," Nature, vol. 405, pp. 458-462 (May 25, 2000).

Brack, et al., "Mechanisms underlying the autonomic modulation of ventricular fibrillation initiation tentative prophylactic properties in vagus nerve stimulation on malignant arrhythmias in heart failure," Heart Fail Rev (Published online Jun. 8, 2012).
Bronzino, "Biomedical Engineering Fundamentals," CRC Press, Chapter 30, pp. 30-10-30-15 (Apr. 2006).
Buschman, et al., "Heart Rate Control Via Vagus Nerve Stimulation," Neuromodulation, vol. 9, No. 3, pp. 214-220 (2006).
Butterwick, et al., "Tissue Damage by Pulsed Electrical Stimulation," IEEE Transactions on Biomedical Engineering, vol. 54, No. 12, pp. 2261-2267 (Dec. 2007).
Calkins, et al., "Comparison of Responses to Isoproterenol and Epinephrine During Head-Up Tilt in Suspected Vasodepressor Syncope," The American Journal of Cardiology, vol. 67 pp. 207-209 (Jan. 15, 1991).
Castoro et al., "Excitation properties of the right cervical vagus nerve in adult dogs," Experimental Neurology, vol. 2 227, iss. 1, pp. 62-68 (Jan. 2011). Online Publication Date: Sep. 17, 2010. Available at: http://www.sciencedirecl.com/science/article/pii/SOO1448861000347X.
Chapleau, et al., "Methods of assessing vagus nerve activity and reflexes," Heart Fail Rev, 16, pp. 109-127 (2011).
Chen, et al., "National and Regional Trends in Heart Failure Hospitalization and Mortality Rates for Medicare Beneficiaries, 1998-2008," JAMA, vol. 306, No. 15 (Oct. 19, 2011).
Chen, et al., "Role of Atrial Electrophysiology and Autonomic Nervous System in Patients with Supraventricular Tachycardia and Paroxysmal Artrial Fibrillation," J Am Coll Cardiol, vol. 32, No. 3, pp. 732-738 (Sep. 1998).
Cheng, et al., "Long-term Outcomes in Individuals with Prolonged PR Interval or First-Degree Atrioventricular Block," JAMA, vol. 301, No. 24 pp. 2571-2577 (Jun. 24, 2009).
Chiou, et al., "Effects of Continuous Enhanced Vagal Tone and Dual Atrioventricular Node and Accessory Pathways," Circulation, Journal of the American Heart Association, 107, pp. 2583-2588 (2003).
Cohen, et al., "Histopathology of the stimulated Vagus nerve: Primum non nocere," Heart Fail Rev, 16, pp. 163-169 (2011).
Colombo, et al., "Comparison between spectral analysis and the phenylephrine methods for the assessment of baroreflex sensitivity in chronic heart failure," Clinical Science, 97, pp. 503-513 (1999).
Cryan, et al., "Animal models and mood disorders: recent developments," Current Opinion in Psychiatry, 20, pp. 1-7 (2007).
Das, "Vagal nerve stimulation in prevention and management of coronary heart disease," World J. Cardiol, 3(4), pp. 105-110 (Apr. 26, 2011).
De Castro, et al., "Parasympathetic-mediated atrial fibrillation during tilt test associated with increased baroreflex sensitivity," The European Society of Cardiology, Europace, 8, pp. 349-351 (2006).
De Ferrari, et al., Chronic Vagus Nerve Stimulation: A New and Promising Therapeutic Approach for Chronic Heart Failure, European Heart Journal, vol. 32, Oct. 28, 2010, pp. 847-855.
De Ferrari, et al., "Baroreflex Sensitivity Predicts Long-Term Cardiovascular Mortality After Myocardial Infarction Even in Patients with Preserved Left Ventricular Function," Journal of the American College of Cardiology, vol. 50, No. 24, pp. 2285-2290 (2007).
De Ferrari, et al., "Chronic Vagal Stimulation in Patients with Congestive Heart Failure," 31st Annual International Conference of the IEE EMBS (2009).
De Ferrari, et al., "Vagus nerve stimulation: from pre-clinical to clinical application: challenges and future directions," Heart Fail Rev, 16, pp. 195-203 (2011) (Published Online Dec. 17, 2010).
De Jonge, et al., "Stimulation of the vagus nerve attenuates macrophage activation by activating the Jak2-STAT3 signaling pathway," Nature Immunology, vol. 6, No. 8, pp. 844-852 (Aug. 2005).
Desai, et al., "Pharmacologic modulation of parasympathetic activity in heart failure," Heart Fail Rev, 16, pp. 179-193 (Published online: Oct. 6, 2010) (2011).
Dickerson, et al., "Parasympathetic neurons in the cranial medial ventricular fat pad on the dog heart selectively decrease ventricular contractility," Journal of the Autonomic Nervous System, 70, pp. 129-141 (1998).

(56) References Cited

OTHER PUBLICATIONS

Dunlap, et al., "Mechanisms of altered vagal control in heart failure: influence of muscarinic receptors and acetylcholinesterase activity," Am J Physiol Heart Gire Physiol, 285, pp. H1632-H1640 (Jun. 26, 2003).

Elsenbruch, et al., "Heart Rate Variability During Waking and Sleep in Healthy Males and Females," Sleep, vol. 22, No. 8, pp. 1067-1071 (1999).

Euler, et al., "Acetylcholine release by a stimulus train lowers atrial fibrillation threshold," Am. J Physiol. 253 (Heart Gire. Physiol, 22), pp. H863-H868 (1987).

Evans, et al., "Histological and functional studies on the fibre composition of the vagus nerve of the rabbit," Journal of Anatomy, 130, pp. 139-151 (1954).

Fallen, "Vagal Afferent Stimulation as a Cardioprotective Strategy? Introducing the Concept," A.N.E., vol. 10, No. 4 (Oct. 2005).

Fan, et al., "Transvenous vagus nerve stimulation: A potential heart failure therapy is feasible in humans," JACC, vol. 55, issue 10A, pp. E152-E153 (2010).

Fazan, et al., "Diabetic Peripheral Neuropathies: A Morphometric Overview," Int. J. Morphol, 28(1), pp. 51-64 (2010).

Feinauer, et al., "Ouabain enhances release of acetylcholine in the heart evoked by unilateral vagal stimulation," Arch Pharmacol, 333, pp. 7-12 (1986).

Fonarow, et al., "Incremental Reduction in Risk of Death Associated with Use of Guideline-Recommended Therapies in Patients with Heart Failure: A Nested Case-Control Analysis of IMPROVE HF," J Am Heart Assoc, 1, pp. 16-26 (2012).

Ford, et al., "The effects of electrical stimulation of myelinated and non-myelinated vagal fibres on heart rate in the rabbit," J. Physiol. 380, pp. 341-347 (1986).

Furukawa, et al., "Effects of Verapamil, Zatebradine, and E-4031 on the Pacemaker Location and Rate in Response to Sympathetic Stimulation in Dog Hearts," The Journal of Pharmacology and Experimental Therapeutics, vol. 289, No. 3, pp. 1334-1342 (1999).

Furukawa, et al., "Selective inhibition by zatebradine and discrete parasympathetic stimulation of the positive chronotropic response to sympathetic stimulation in anesthetized dogs," Abstract, Journal of Pharmacology & Experimental Therapeutics, 272(2):744-9 (1995).

Gatti, et al., "Can neurons in the nucleus ambiguous selectively regulate cardiac rate and atrioventricular conduction?" Journal of the Autonomic Nervous System, 57, pp. 123-127 (1996).

Gatti, et al., "Vagal control of left ventricular contractility is selectively mediated by a cranioventricular intracardiac ganglion in the cat," Journal of the Autonomic Nervous System, 66, pp. 138-144 (1997).

Gibbons, et al., "Neuromodulation targets intrinsic cardiac neurons to attenuate neuronally mediated atrial arrhythmias," Am J Physiol Regul Integr Comp Physiol 302: R357-R364 (2012) (First published Nov. 16, 2011).

Gottdiener, et al., "Predictors of Congestive Heart Failure in the Elderly: The Cardiovascular Health Study," Journal of the American College of Cardiology, vol. 35, No. 6, pp. 1628-1637 (2000).

Gray, et al., "Parasympathetic control of the Heart. II. A novel interganglionic intrinsic cardiac circuit mediates neural control of heart rate," J. Appl Physiol, 96, pp. 2273-2278 (2004).

Gray, et al., "Parasympathetic control of the Heart. III. Neuropeptide Y-immunoreactive nerve terminals synapse on three populations of negative chronotropic vagal preganglionic neurons," J. Appl Physiol, 96, pp. 2279-2287 (2004).

Grill, "Chapter 14—Principles of Electric Field Generation for Stimulation of the Central Nervous System," Neuromodulation, Academic Press (2009).

Guilleminault, et al., "Cyclical Variation of the Heart Rate in Sleep Apnea Syndrome," The Lancet, pp. 126-131 (Jan. 21, 1984).

Hardwick, et al., "Chronic myocardial infarction induces phenotypic and functional remodeling in the guinea pig cardiac plexus," Am J Physiol Regulatory Integrative Comp Physiol, 295, pp. 1926-1933 (2008).

Hardwick, et al., "Remodeling of the guinea pig intrinsic cardiac plexus with chronic pressure overload," Am J Physiol Regulatory Integrative Comp Physiol, 297, pp. 859-866 (2009).

Hauptman, et al., "The vagus nerve and autonomic imbalance in heart failure: past, present, and future," Heart Fail Rev, 16, pp. 97-99 (2011).

Hellyer, et al., "Autonomic nerve activity and blood pressure in ambulatory dogs," Heart Rhythym, vol. 11(2), pp. 307-313 (Feb. 2014).

Hirooka, et al., "Imbalance of central nitric oxide and reactive oxygen species in the regulation of sympathetic activity and neural mechanisms of hypertension," Am J Physiol Regulatory Integration Comp Physiol, 300, pp. 818-826 (2011).

Hoffman, et al., "Vagus Nerve Components," Anat Rec, 127, pp. 551-568 (1957).

Hu, et al., "Role of sympathetic nervous system in myocardial ischemia injury: Beneficial or deleterious?" Letters to the Editor, Elsevier Ireland Ltd. (Mar. 27, 2012).

Hua, et al., "Left vagal stimulation induces dynorphin release and suppresses substance P release from the rat thoracic spinal cord during cardiac ischemia," Am J Physiol Regulatory Integration Comp Physiol, 287, pp. 1468-1477 (2004).

Huston, et al., "Splenectomy inactivates the cholinergic antiinflammatory pathway during lethal endotoxemia and polymicrobial sepsis," J. Exp. Med, vol. 203, No. 7 pp. 1623-1628 (Jun. 19, 2006).

Huston, et al., "Transcutaneous vagus nerve stimulation reduces serum high mobility group box 1 levels and improves survival in murine sepsis," Grit Care Med, vol. 35, No. 12, pp. 2762-2768 (2007).

Ingemansson, et al., "Autonomic modulation of the atrial cycle length by the head up tilt test: noninvasive evaluation in patients with chronic atrial fibrillation," Heart, 80, pp. 71-76 (1998).

International Search Report for PCT Patent Application No. PCT/US2015/060200, dated Feb. 8, 2016, 14 pages.

Ito, et al., "Efferent sympathetic and vagal innervation of the canine right ventricle," Circulation, Journal of the American Heart Association, vol. 90, pp. 1469-1468 (1994).

Jacques, et al., "Spinal Cord Stimulation Causes Potentiation of Right Vagus Nerve Effects on Atrial Chronotropic Function and Repolarization in Canines," Journal of Cardiovascular Electrophysiology, vol. 22, No. 4, pp. 440-447 (Apr. 2011).

Jaenisch, et al., "Respiratory muscle training improves baroreceptor sensitivity, decrease sympathetic tonus and increase vagal effect in rats with heart failure," European Heart Journal, 32 (Abstract Supplement, pp. 976 (2011).

Jammes, et al., "Afferent and efferent components of the bronchial vagal branches in cats," Journal of the Autonomic Nervous System, 5, pp. 165-176 (1982).

Janabi, et al., "Oxidized LDL-Induced NF-kB Activation and Subsequent Expression of Proinflammatory Genes are Defective in Monocyte-Derived Macrophages from CD36-Deficient Patients," Arterioscler Thromb Vase Biol., 20:1953-1960 (2000).

Janse, et al., "Effects of unilateral stellate ganglion stimulation and ablation on electrophysiologic changes induced by acute myocardial ischemia in dogs," Circulation, Journal of the American Heart Association, 72, pp. 585-595 (1985).

Jessup; et al., "2009 Focused Update: ACCF/AHA Guidelines for the Diagnosis and Management of Heart Failure in Adults," Circulation, Journal of the American Heart Association, vol. 119, pp. 1977-2016 (2009).

Johnson, et al., "Parasympathetic control of the heart. I. An interventriculo-septal ganglion is the major source of the vagal intracardiac innervation of the ventricles," J Appl Physiol, 96, pp. 2265-2272 (2004).

Kakinuma, et al., "Cholinoceptive and cholinergic properties of cardiomyocytes involving an amplification mechanism for vagal efferent effects in sparsely innervated ventricular myocardium," FEBS Journal, 276, pp. 5111-5125 (2009).

Kalman, "Specific effects of zatebradine on sinus node function: suppression of automaticity, prolongation of sinoatrial conduction and pacemaker shift in the denervated canine heart," Abstract, Journal of Pharmacology & Experimental Therapeutics, 272(1):85-93 (1995).

(56) References Cited

OTHER PUBLICATIONS

Kaneko, et al., "C-Reactive Protein in Dilated Cardiomyopathy," Cardiology, 91, pp. 215-219 (1999).
Katare, et al., "Vagal nerve stimulation prevents reperfusion injury through inhibition of opening of mitochondrial permeability transition pore independent of bradycardiac effect," The Journal of Thoracic and Cardiovascular Surgery, vol. 137, No. 1, pp. 223-231 (2009).
Katz, et al., "Diseases of the heart in the Works of Hippocrates," Br Heart J, 24, pp. 257-264 (1962).
Kawada, et al., "High-frequency dominant depression of peripheral vagal control of heart rate in rats with chronic heart failure," Acta Physiol 207, 494-502 (2013).
Kawada, et al., "Vagal stimulation suppresses isschemia-induced myocardial interstitial norepinephrine release," Life Sciences, 78, pp. 882-887 (2006).
Kawashima, "The autonomic nervous system of the human heart with special reference to its origin, course, and peripheral distribution," Anat Embryol, 209, pp. 425-438 (2005).
Klein et al., "Vagus nerve stimulation: A new approach to reduce heart failure," Cardiology Journal, vol. 17, iss. 6, pp. 638-643 (2010).
Kliks, et al., "Influence of Sympathetic Tone on Ventricular Fibrillation Threshold During Experimental Coronary Occlusion," The American Journal of Cardiology, vol. 36, pp. 45-49 (Jul. 1975).
Kolman, et al., "The effect of vagus nerve stimulation upon vulnerability of the canine ventricle: role of sympathetic-parasympathetic interactions," Journal of the American Heart Association, 52, pp. 578-585 (1975).
Kong, et al., "Optimizing the Parameters of Vagus Nerve Stimulation by Uniform Design in Rats with Acute Myocardial Infarction," PLOS One, vol. 7, issue 11 (Nov. 2012).
Koopman, et al., "Pilot study of stimulation of the cholinergic anti-inflammatory pathway with an implantable vagus nerve stimulation device in patients with rheumatoid arthritis," Abstract (2012).
Kulbertus, et al., ed., "Neurocardiology," Future Publishing Co., pp. 13 ("Anatomy of the Cardiac Efferent Innvervation"); 61-63 ("Autonomic Neural Control"); 87, 89, 92-93 ("Sympathetic-Parasympathetic Interactions"); 183, 187 ("Parasympathetic Nervous System"); 104 (1988).
La Rovere, et al., "Baroreflex Sensitivity and Heart Rate Variability in the Identification of Patients at Risk for Life-Threatening Arrhythmias: Implications for Clinical Trials," Circulation, Journal of the American Heart Association, 103, pp. 2072-2077 (2001).
Lane, et al., "Prediction and Prevention of Sudden Cardiac Death in Heart Failure," Heart, 91, pp. 674-680 (2005).
Lechat, et al., "Heart rate and Cardiac Rhythm Relationships with Bisoprolol Benefit in Chronic Heart Failure in CIBIS II Trial," Circulation, Journal of American Heart Association, 103, pp. 1428-1433 (2001).
Lewis, et al., "Vagus nerve stimulation decreases left ventricular contractility in vivo in the human and pig heart," Journal of Physiology, 534, pp. 547-552 (2001).
Li et al., "Vagal Nerve Stimulation Markedly Improves Long-Term Survival After Chronic Heart Failure in Rats," Circulation: Journal of the American Heart Association, vol. 109, iss. 1, pp. 120-124 (Jan. 2004). Online publication date: Dec. 8, 2003.
Li, et al., "Early vagal stimulation markedly prevented cardiac dysfunction in rats after acute myocardial infarction in addition to suppressing arrhythmic death," European Heart Journal, 32 (Abstract Supplement), pp. 297-298 (2011).
Li, et al., "Inflammatory cytokines and nitric oxide in heart failure and potential modulation by vagus nerve stimulation," Heart Fail Rev, 16, pp. 137-145 (2011).
Li, et al., "Low-Level Vagosympathetic Stimulation. A Paradox and Potential New Modality for the Treatment of Focal Atrial Fibrillation," Gire Arrhythm Electrophysiol, Journal of American Heart Association, 2, pp. 645-651 (2009).
Li, et al., "Restoration of vagal tone by donepezil, on top of losartan treatment, markedly suppresses ventricular dysfunction and improves long-term survival in chronic heart failure rats," European Heart Journal, 32 (Abstract Supplement), pp. 642 (2011).
Libby, et al., "Inflammation and Atherosclerosis," Circulation, Journal of the American Heart Association, 105, pp. 1135-1143 (2002).
Liu, et al., "Differing sympathetic and vagal effects on atrial fibrillation in dogs: role of refractoriness heterogeneity," Am. J. Physiol. 273 (Heart Gire. Physiol. 42), pp. H805-H816 (1997).
Lo, et al., "Paradoxical long-term proarrhythmic effects after ablating the 'head station' ganglionated plexi of the vagal innervation to the heart," Heart Rhythm, vol. 10, No. 5, pp. 751-757 (May 2013).
Lohmeier, et al., "Prolonged Activation of the Barorelfex Produces Sustained Hypotension," Hypertension, Journal of the American Heart Association, 43, pp. 306-311 (2004).
Lu, et al., "Vagal nerve stimulation protects cardiac injury by attenuating mitochondria) dysfunction in a murine burn injury model," J. Cell. Mol. Med., vol. 17, No. 5, pp. 664-671 (2013).
Ma, et al., "Analysis of afferent, central, and efferent components of the baroreceptor reflex in mice," Am J Physiol Regulatory Integration Comp Physiol, 283, pp. 1033-1040 (2002).
Maj, et al., "P5775: Autonomic imbalance and circulating androgens and estrogens in men with systolic heart failure," European Heart Journal, 32 (Abstract Supplement), pp. 1090 (2011).
Malkin, et al., "Life-saving or life-prolonging? Interpreting trial data and survival curves for patients with congestive heart failure," The European Journal of Heart Failure, 7, pp. 143-148 (2005).
Mann, "Chapter 12—Peripheral Nerves," The Nervous System in Action, michaeldmann.net/mannl2.html, (Jul. 2011).
Mann, "Inflammatory Mediators and the Failing Heart. Past, Present, and the Foreseeable Future," Circ Res., 91, pp. 988-998 (2002).
Mann, "Stress-Activated Cytokines and the Heart: From Adaptation to Maladaptation," Annu. Rev. Physiol., 65, pp. 81-101 (2003).
Martin-Portugues, et al., "Histopathologic features of the vagus nerve after electrical stimulation in swine," Histol Histopathol, 20, pp. 851-856 (2005).
Martins, et al., "Distribution of Local Repolarization Changes Produced by Efferent Vagal Stimulation in the Canine Ventricles," JACC, vol. 2, No. 6, pp. 1191-1199 (Dec. 1983).
Massari, et al., "Neural control of left ventricular contractility in the dog heart: synaptic interactions of negative inotropic vagal preganglionic neurons in the nucleus ambiguus and tyrosine hydroxylase immunoreactive terminals," Brain Research, 802, pp. 205-220 (1998).
May, et al., "P564: Long-term prediction of all-cause mortality in diabetic autonomic neuropathy: simple function tests or 24-hour heart rate variability (HRV)?" European Heart Journal, 32 (Abstract Supplement, pp. 64 (2011).
Mei, et al., "The Composition of the Vagus Nerve of the Cat," Cell Tissue Res., 209, pp. 423-431 (1980).
Merrill, et al., "Electrical stimulation of excitable tissue: design of efficacious and safe protocols," Journal of Neuroscience Methods, 141, pp. 171-198 (2005).
Mortara, et al., "Arterial Baroreflex Modulation of Heart Rate in Chronic Heart Failure," Circulation, Journal of the American Heart Association, vol. 96, No. 10, pp. 3450-3458 (Nov. 18, 1997).
Murakawa, et al., "Effect of Cervical Vagal Nerve Stimulation on Defibrillation Energy," Jpn Heart J, 44, pp. 91-100 (Jan. 2003).
Naito, "Effects of zatebradine and propranolol on canine ischemia and reperfusion-induced arrhythmias," European Journal of Pharmacology, 388, pp. 171-176 (2000).
Nakajima, et al., "Autonomic Control of the Location and Rate of the Cardiac Pacemaker in the Sinoatrial Fat Pad of Parasympathetically Denervated Dog Hearts," Journal of Cardiovascular Electrophysiology, vol. 13, No. 9 pp. 896-901 (Sep. 2002).
Nearing, et al., "Crescendo in Depolarization and Repolarization Heterogeneity Heralds Development of Ventricular Tachycardia in Hospitalized Patients with Decompensated Heart Failure," Circulation Arrhythmia and Electrophysiology, Journal of the American Heart Association, 5, pp. 84-90 (2012).
Nihei, et al., "Decreased Vagal Control Over Heart Rate in Rats with Right-Sided Congestive Heart Failure —Downregulation of Neuronal Nitric Oxide Synthase," Gire J, 69, pp. 493-499 (2005).
Ninomiya, "Direct Evidence of Nonuniform Distribution of Vagal Effects on Dog Atria," Circulation Research, vol. XIX, pp. 576-583 (Sep. 1966).

(56) References Cited

OTHER PUBLICATIONS

Nolan, et al., "Prospective Study of Heart Rate Variability and Mortality in Chronic Heart Failure: Results of the United Kingdom Heart Failure Evaluation and Assessment of Risk Trial (UK—Heart)," Circulation, Journal of the American Heart Association, 98, pp. 1510-1516 (1998).
Ochoa, et al., "P2497: Effects of insulin resistance on resting heart rate, baroreflex sensitivity and indices of autonomic cardiovascular modulation in individuals with high blood pressure levels," European Heart Journal, 32 (Abstract Supplement, pp. 431-432 (2011).
Ogawa, et al., "Left Stellate Ganglion and Vagal Nerve Activity and Cardiac Arrhythmias in Ambulatory Dogs with Pacing-Induced Congestive Heart Failure," Journal of the American College of Cardiology, vol. 50, No. 4, pp. 335-444 (2007).
Okada, et al., "Cyclic Stretch Upregulates Production of Interleukin-8 and Monocyte Chemotactic and Activating Factor/Monocyte Chemoattractant Protein-1 in Human Endothelial Cells," Arterioscler Thromb Vase Biol., 18, pp. 894-901 (1998).
Oliveira, et al., "Effects of vagal stimulation on induction and termination of atrial fibrillation in an in vivo rabbit heart model," Rev Port Cardiol, 29(03), pp. 375-389 (2010).
Olshansky, et al., "Parasympathetic Nervous System and Heart Failure: Pathophysiology and Potential Implications for Therapy," Circulation, Journal of the American Heart Association, 118, pp. 863-871 (2008).
Onkka, et al., "Sympathetic nerve fibers and ganglia in canine cervical vagus nerves: Localization and quantitation," Heart Rhythm, vol. 10, No. 4, pp. 585-591 (Apr. 2013).
Ordelman, et al., "Selectivity for Specific Cardiovascular Effects of Vagal Nerve Stimulation with a Multi-Contact Electrode Cuff," IEEE, pp. 1-6 (2011).
Packer, et al., "Effect of Carvedilol on Survival in Severe Chronic Heart Failure," The New England Journal of Medicine, vol. 344, No. 22, pp. 1651-1658 (May 31, 2001).
Pavlov, et al., "Central muscarinic cholinergic regulation of the systemic inflammatory response during endotoxemia," PNAS, vol. 103, No. 13, pp. 5219-5223 (Mar. 28, 2006).
Pavlov, et al., "Controlling inflammation: the cholinergic anti-inflammatory pathway," Biochemical Society Transactions, vol. 34, part 6, pp. 1037-1040 (2006).
PCT Application No. PCT/US2012/068205, Search Report and Written Opinion dated Feb. 8, 2013, 15 pages.
PCT Application No. PCT/US2012/068211, Search Report and Written Opinion dated Jun. 13, 2013.
PCT Application No. PCT/US2012/068223, Search Report and Written Opinion dated Apr. 3, 2013, 11 pages.
PCT Application No. PCT/US20121068213, Search Report and Written Opinion dated Mar. 15, 2013, 11 pages.
PCT Application No. PCT/US2013/021964, Search Report and Written Opinion dated Jul. 25, 2013, 9 pages.
PCT Application No. PCT/US2013/050390, Search Report and Written Opinion dated Nov. 5, 2013.
PCT Application No. PCT/US2013/068541, Search Report and Written Opinion dated Jan. 7, 2014.
PCT Application No. PCT/US2014/024827, Search Report and Written Opinion dated Nov. 11, 2014, 18 pages.
PCT Application No. PCT/US2015/020116, Search Report and Written Opinion dated Jul. 6, 2015, 12 pages.
Peckham, et al., "Chapter 18—Implantable Neural Stimulators," Neuromodulation, Academic Press (2009).
Pina, et al., "The Predictive Value of Biomarkers in Heart Failure," Medscape Education Cardiology, Available at http://www.medscape.org/viewarticle/765328 (CME Released: Jun. 15, 2012).
Pitzalis, et al., "Comparison Between Noninvasive Indices of Baroreceptor Sensitivity and the Phenylephrine Method in Post-Myocardial Infarction Patients," Circulation, Journal of the American Heart Association, 97, pp. 1362-1367 (1998).
Poole-Wilson, "Relation of Pathophysiologic Mechanisms to Outcome in Heart Failure," JACC, vol. 22, No. 4 (supplement A), pp. 22A-29A (Oct. 1993).
Pye, et al., "Study of serum C-reactive protein concentration in cardiac failure," Br Heart J, 63, pp. 228-230 (1990).
Rademacher, et al., "P5878: Multidimensional halter-based analysis of cardiac autonomic regulation predicts early AF recurrence after electrical cardioversion," European Heart Journal, 32 (Abstract Supplement), pp. 1116-1117 (2011).
Randall, et al., "Regional vagosympathetic control of the heart," American Journal of Physiology, vol. 227, No. 2, pp. 444-452 (1974).
Randall, et al., "Selective Vagal Innervation of the Heart," Annals of Clinical and Laboratory Science, vol. 16, No. 3, pp. 198-208 (1986).
Raymond, et al., "Elevated interleukin-6 levels in patients with asymptomatic left ventricular systolic dysfunction," American Heart Journal, vol. 141, No. 3, pp. 435-438 (Mar. 2001).
Rhee, et al., "Effects of suprathreshold vagal stimulation on stellate ganglion nerve activity in ambulatory dogs," 33rd Annual Scientific Sessions, Heart Rhythm, Presentation Abstract (2012).
Riccio, et al., "Interganglionic segregation of distinct vagal afferent fibre phenotypes in guinea-pig airways," Journal of Physiology, 495.2, pp. 521-530 (1996).
Riddle, et al., "Epidemiologic Relationships Between A1C and All-Cause Mortality During a Median 3.4-Year Follow-up of Glycemic Treatment in the ACCORD Trial," Diabetes Care, vol. 33, No. 5, pp. 983-990 (May 2010).
Ridker, C-Reactive Protein: A Simple Test to Help Predict Risk of Heart Attack and Stroke, Journal of the American Heart Association, 108, pp. e81-e85 (2003).
Ridker, et al., "Comparison of C-Reactive Protein and Low-Density Lipoprotein Cholesterol Levels in the Prediction of First cardiovascular Events," New England Journal of Medicine, vol. 347, No. 20, pp. 1557-1566 (Nov. 14, 2002).
Ridker, et al., "C-Reactive Protein and Other Markers of Inflammation in the Prediction of Cardiovascular Disease in Women," The New England Journal of Medicine, vol. 342, No. 12, pp. 836-841 (Mar. 23, 2000).
Ridker, et al., "Inflammation, Pravastatin, and the Risk of Coronary Events After Myocardial Infarction in Patients With Average Cholesterol Levels," Circulation, Journal of the American Heart Association, 98, pp. 839-844 (1998).
Roger, et al., "Heart Disease and Stroke Statistics—2011 Update: A Report from the American Heart Association," Circulation, Journal of the American Heart Association. Available at http://circ.ahajournals.org/content/123/4/e18 (2010).
Romanovsky, et al., "The vagus nerve in the thermoregulatory response to systemic inflammation," Am. J. Physiol., 273, pp. R407-R413 (1997).
Rossi, et al., "Epicardial ganglionated plexus stimulation decreases postoperative inflammatory response in humans," Heart Rhythm, vol. 9, No. 6, pp. 943-950 (Jun. 2012).
Rouse, et al., "The haemodynamic actions of ZENCA ZD7288, a novel sino-atrial node function modulator, in the exercising beagle: a comparison with zategradine and propranolol," Abstract, British Journal of Pharmacology, 113(3):1071-7 (1994).
Rozman, et al., "Heart function influenced by selective mid-cervical left vagus nerve stimulation in a human case study," Hypertension Research, 32, pp. 1041-1043 (2009).
Rutecki, "Anatomical, Physiological and Theoretical Basis for the Antiepileptic Effect of Vagus Nerve Stimulation," Epilepsia, 31 (suppl. 2), pp. S1-S6 (1990).
Sabbah et al., "Vagus Nerve Stimulation in Experimental Heart Failure," Heart Failure Reviews, vol. 16, No. 2, Mar. 2011, pp. 171-178.
Sabbah, et al., "3722: Vagus nerve stimulation improves left ventricular function in heart failure: results of a 6 month investigation with a cross-over design in dogs with experimental heart failure," European Heart Journal, 32 (Abstract Supplement), pp. 642 (2011).
Sabbah, et al., "Baroreflex Activation Therapy for the Treatment of Heart Failure," Presentation available at http://www.cvrx.com/wp/wp-contenUuploads/2012/04/Dr.-Sabbah-Slides.pdf (2012).
Sabbah, et al., "Chronic Electrical Stimulation of the Carotid Sinus Baroreflex Improves Left Ventricular Function and Promotes Reversal of Ventricular Remodeling in Dogs with Advanced Heart Fail-

(56) References Cited

OTHER PUBLICATIONS ure," Circulation Heart Failure, Journal of the American Heart Association, 4, pp. 65-70 (2011).
Samara, et al., "The Effects of Cardiac Resynchronization Therapy on Chronotropic Incompetence in Patients Intolerant of Beta Antagonist Therapy," Journal of Cardiac Failure, vol. 17, No. 8S, pp. S54-S55 (Aug. 2011).
Sanner, et al., "P4743: Prediction of cardiovascular risk from nocturnal pulse wave signal using the autonomic state indicator (ASI) technology," European Heart Journal, 32 (Abstract Supplement), pp. 839 (2011).
Sato, et al., "Serial Circulating Concentrations of C-Reactive Protein, Interleukin (IL)-4, and IL-6 in Patients with Acute Left Heart Decompensation," Clin. Cardiol. 22, pp. 811-813 (1999).
Schauerte, "Time for Change: Cardiac neurophysiology meets cardiac electrophysiology," Editorial Commentary, Heart Rhythm Society (2013).
Schiereck, et al., "AV blocking due to asynchronous vagal stimulation in rats," Am J Physiol Heart Gire Physiol, 278, pp. H67-H73 (2000).
Schocken, et al., "Prevalence and Mortality Rate of Congestive Heart Failure in the United States," JACC, vol. 20, No. 2, pp. 301-306 (Aug. 1992).
Schwartz, "Vagal Stimulation for Heart Diseases: From Animals to Men," Circulation Journal, vol. 75, pp. 20-27 (Jan. 2011).
Schwartz, "Vagal stimulation for heart failure," Current Opinion in Cardiology, 26, pp. 51-54 (2011).
Schwartz, "Vagal stimulation for the treatment of heart failure: a translational success story," Heart, vol. 98, No. 23, pp. 1687-1690 (2012).
Schwartz, et al. Vagal stimulation for heart failure: Background and first in-man study, Heart Rhythm, 6, 11 suppl., pp. S76-81 (Nov. 2009).
Schwartz, et al., "Autonomic mechanisms and sudden death. New insights from analysis of baroreceptor reflexes in conscious dogs with and without myocardial infarction," Circulation, Journal of the American Heart Association, 78, pp. 969-979 (1988).
Schwartz, et al., "Effects of Unilateral Cardiac Sympathetic Denervation on the Ventricular Fibrillation Threshold," The American Journal of Cardiology, vol. 37, pp. 1034-1040 (Jun. 1976).
Schwartz, et al., "Long term vagal stimulation in patients with advanced heart failure. First experience in man," European Journal of Heart Failure, 10, pp. 884-891 (2008).
Schwartz, et al., "Sympathetic-parasympathetic interaction in health and disease: abnormalities and relevance in heart failure," Heart Fail Rev, 16, pp. 101-107 (2011).
Seta, et al., "Basic Mechanisms in Heart Failure: The Cytokine Hypothesis," Journal of Cardiac Failure, vol. 2, No. 3, pp. 243-249 (1996).
Sha, et al., "Low-Level Right Vagal Stimulation: Anticholinergic and Antiadrenergic Effects," J Cardiovasc Electrophysiol, pp. 1-7 (Feb. 2011).
Shamoon, et al., The Diabetes Control and Complications Trial Research Group, "The effect of intensive treatment of diabetes on the development and progression of long-term complications in insulin-dependent diabetes mellitus," The New England Journal of Medicine, vol. 329, No. 14, pp. 977-986 (Sep. 30, 1993).
Shannon, "A Model of Safe Levels for Electrical Stimulation," IEEE Transactions on Biomedical Engineering, vol. 39, No. 4, pp. 424-426 (Apr. 1992).
Shen, et al., "Continuous Low-Level Vagus Nerve Stimulation Reduces Stellate Ganglion Nerve Activity and Paroxysmal Atrial Tachyarrhythmias in Ambulatory Canines," Circulation, Journal of the American Heart Association, 123, pp. 2204-2212 (2011).
Shen, et al., "Low-level vagus nerve stimulation upregulates small conductance calcium-activated potassium channels in the stellate ganglion," Heart Rhythm, vol. 10, No. 6, pp. 910-915 (2013).
Shinohara, et al., "Heart Failure Decreases Nerve Activity in the Right Atrial Ganglionated Plexus," J Cardiovasc Electrophysiol, pp. 1-9 (2011).

Shioi, et al., "Increased Expression of Interleukin-1B and Monocyte Chemotactic and Activating Factor/Monocyte Chemoattractant Protein-1 in the Hypertrophied and Failing Heart with Pressure Overload," Gire Res., 81, pp. 664-671 (1997).
Singal, et al., "The role of oxidative stress in the genesis of heart disease," Cardiovascular Research, 40, pp. 426-432 (1998).
Spuck, et al., "Right-sided vagus nerve stimulation in humans: An effective therapy?" Epilepsy Research, pp. 1-3 (2008).
Stein, et al., "A Simple Method to Identify Sleep Apnea Using Holter Recordings," J Cardiovasc Electrophysiol, vol. 14, pp. 467-473 (May 2003).
Stein, et al., "Feasibility of Using Mobile Cardiac Outpatient Telemetry (MCOT) to Identify Severe Sleep Disorders" (2009).
Stieber, et al., "Bradycardic and proarrhythmic properties of sinus node inhibitors," Abstract, Molecular Pharmacology, 69(4):1328-37 (2006).
Taylor, et al., "The unequal influences of the left and right vagi on the control of the heart and pulmonary artery in the rattlesnake, Grata/us durissus," The Journal of Experimental Biology, 212, pp. 145-151 (2009).
Thayer, et al., "The role of vagal function in the risk for cardiovascular disease and mortality," Biological Psychology, 74, pp. 224-242 (2007).
Thollon, et al., "Electrophysiological effects of S 16257, a novel sino-atrial node modulator, on rabbit and guinea-pig cardiac preparations: comparison with UL-FS 49," Abstract, British Journal of Pharmacology, 112(1):37-42 (1994).
Tosato, et al., "Quasi-trapezoidal pulses to selectively block the activation of intrinsic laryngeal muscles during vagal nerve stimulation," J. Neural Eng., 4, pp. 205-212 (2007).
Tsutsumi, et al., "Modulation of the myocardial redox state by vagal nerve stimulation after experimental myocardial infarction," Cardiovascular Research, 77, pp. 713-721 (2008).
Tyler, et al., "Chapter 17—Electrodes for the Neural Interface," Neuromodulation, Academic Press (2009).
Ulphani, et al., "Quantitative analysis of parasympathetic innervation of the porcine heart," Heart Rhythm, 7, pp. 1113-1119 (2010).
Uthman, et al., "Effectiveness of vagus nerve stimulation in epilepsy patients. A 12-year observation," Neurology, 63, pp. 1124-1126 (2004).
Van Stee, "Autonomic Innervation of the Heart," Environmental Health Perspectives, vol. 26, pp. 151-158 (1978).
Vanoli, et al., "Vagal stimulation and prevention of sudden death in conscious dogs with a healed myocardial infarction," Circulation Research, Journal of the American Heart Association, 68, pp. 1471-1481 (1991).
Vasan, et al., "Inflammatory Markers and Risk of Heart Failure in Elderly Subjects Without Prior Myocardial Infarction," Circulation, Journal of the American Heart Association, 107, pp. 1486-1491 (2003).
Vassalle, et al., "An Analysis of Arrhythmias Induced by Ouabain in Intact Dogs," Circulation Research, Journal of the American Heart Association, 13, pp. 132-148 (1963).
Velagaleti, et al., "Long-Term Trends in the Incidence of heart Failure After Myocardial Infarction," 118, pp. 2057-2062 (2008).
Verrier, et al., "Microvolt T-Wave Alternans," Journal of the American College of Cardiology, vol. 58, No. 13, pp. 1309-1324 (2011).
Vimercati, et al., "Acute vagal stimulation attenuates cardiac metabolic response to B-adrenergic stress," The Journal of Physiology, vol. 500, No. 23, pp. 6065-6074 (2012).
Wang, et al., "Nicotinic acetylcholine receptor alpha-7 subunit is an essential regulator of inflammation," Nature, vol. 421, pp. 384-388 (Jan. 23, 2003).
Wang, et al., "Synaptic and Neurotransmitter Activation of Cardiac Vagal Neurons in the Nucleus Ambiguus," Annals New York Academy of Sciences, pp. 237-246 (2001).
Waninger, et al., "Characterization of Atrioventricular Nodal Response to Electrical Left Vagal Stimulation," Annals of Biomedical Engineering, vol. 27, pp. 758-762 (1999).
Wann, "Behavioural signs of depression and apoptosis in the limbic system following myocardial infarction: effects of sertraline," Journal of Psychopharmacology, 23(4), pp. 451-459 (2009).

(56) References Cited

OTHER PUBLICATIONS

Wann, et al., "Vulnerability for apoptosis in the limbic system after myocardial infarction in rats: a possible model for human postinfarct major depression," J Psychiatry Neurosci, 32(1):11-6, pp. 11-16 (2007).

Watkins, et al., "Cytokine-to-Brain Communication: A Review & Analysis of Alternative Mechanisms," Life Sciences, vol. 57, No. 11, pp. 1011-1026 (1995).

Whyte, et al., "Reactive oxygen species modulate neuronal excitability in rat intrinsic cardiac ganglia," Auton Neurosci, 150(1-2), pp. 45-52 (Oct. 5, 2009).

Yang, et al., "Sustained increases in heart rate induced by time repetition of vagal stimulation in dogs," Am. J. Physiol., 249, pp. H703-H709 (1985).

Yin, et al., "Independent prognostic value of elevated high-sensitivity C-reactive protein in chronic heart failure," American Heart Journal, vol. 147, No. 5, pp. 931-938 (2004).

Yndestad, et al., "Systemic inflammation in heart failure—The whys and wherefores," Heart Fail Rev, 11, pp. 83-92 (2006).

Yoo, et al., "High-resolution measurement of electrically-evoked vagus nerve activity in the anesthetized dog," J. Neural Eng., 10, pp. 1-9 (2013).

Yoo, et al., "Selective Control of Physiological Responses by Temporally-Patterned Electrical Stimulation of the Canine Vagus Nerve," 33rd Annual International Conference of the IEEE EMBS (2011).

Yu, et al., "Interactions between atrial electrical remodeling and autonomic remodeling: How to break the vicious cycle," Heart Rhythm, 9, pp. 804-809 (2012).

Yu, et al., "Low-level transcutaneous electrical stimulation of the auricular branch of the vagus nerve: A noninvasive approach to treat the initial phase of atrial fibrillation," Heart Rhythm, 10, pp. 428-435 (2013).

Yuan, et al., "Gross and Microscopic Anatomy of the Canine Intrinsic Cardiac Nervous System," The Anatomical Record, 239, pp. 75-87 (1994).

Yusuf, et al., "Changes in Hypertension Treatment and in Congestive Heart Failure Mortality in the United States," Hypertension, Journal of the American Heart Association, 13:174-1179 (1989).

Zhang, et al., "Arrhythmias and vagus nerve stimulation," Heart Fail Rev, 16, pp. 147-161 (2011).

Zhang, et al., "Involvement of activated astrocyte and microglia of locus coeruleus in cardiac pain processing after acute cardiac injury," Neurol Res, 31, pp. 432-438 (2009).

Zhang, et al., "Relationship between right cervical vagus nerve stimulation and atrial fibrillation inducibility: Therapeutic intensities do not increase arrhythmogenesis," Heart Rhythm, 6, pp. 244-250 (2009).

Zhang, et al., "Therapeutic Effects of Selective Atrioventricular Node Vagal Stimulation in Atrial Fibrillation and Heart Failure," Journal of Cardiovascular Electrophysiology, vol. 24, Issue 1, pp. 86-91 (2012).

Zheng, et al., "Vagal stimulation markedly suppresses arrhythmias in conscious rats with chronic heart failure after myocardial infarction," Proceedings of the 2005 IEEE (2005).

Zipes, et al., "Effects of selective vagal and stellate ganglion stimulation on atrial refractoriness," Cardiovascular Research, 8, pp. 647-655 (1974).

Zucker, et al., "Chronic Baroreceptor Activation Enhances Survival in Dogs with Pacing-Induced Heart Failure," Journal of the American Heart Association, Hypertension (2007).

La Rovere, et al., "Baroreflex sensitivity and heart-rate variability in prediction of total cardiac mortality after myocardial infarction. ATRAMI (Autonomic Tone and Reflexes After Myocardial Infarction) Investigators," Lancet, 351(9101), pp. 478-484 (Feb. 14, 1998).

* cited by examiner

20

NEUROSTIMULATION TITRATION PROCESS VIA ADAPTIVE PARAMETRIC MODIFICATION

CROSS-REFERENCE TO RELATED PATENT APPLICATIONS

The present application is a continuation of U.S. patent application Ser. No. 14/563,181, filed Dec. 8, 2014, which claims priority to and the benefit of U.S. Provisional Patent Application No. 62/078,600, filed Nov. 12, 2014, both of which are incorporated herein by reference in their entireties.

FIELD

This application relates to neuromodulation and, more specifically, to improved systems and methods for titrating stimulation therapies.

BACKGROUND

Chronic heart failure (CHF) and other forms of chronic cardiac dysfunction (CCD) may be related to an autonomic imbalance of the sympathetic and parasympathetic nervous systems that, if left untreated, can lead to cardiac arrhythmogenesis, progressively worsening cardiac function and eventual patient death. CHF is pathologically characterized by an elevated neuroexitatory state and is accompanied by physiological indications of impaired arterial and cardiopulmonary baroreflex function with reduced vagal activity.

CHF triggers compensatory activations of the sympathoadrenal (sympathetic) nervous system and the renin-angiotensin-aldosterone hormonal system, which initially helps to compensate for deteriorating heart-pumping function, yet, over time, can promote progressive left ventricular dysfunction and deleterious cardiac remodeling. Patients suffering from CHF are at increased risk of tachyarrhythmias, such as atrial fibrillation (AF), ventricular tachyarrhythmias (ventricular tachycardia (VT) and ventricular fibrillation (VF)), and atrial flutter, particularly when the underlying morbidity is a form of coronary artery disease, cardiomyopathy, mitral valve prolapse, or other valvular heart disease. Sympathoadrenal activation also significantly increases the risk and severity of tachyarrhythmias due to neuronal action of the sympathetic nerve fibers in, on, or around the heart and through the release of epinephrine (adrenaline), which can exacerbate an already-elevated heart rate.

The standard of care for managing CCD in general continues to evolve. For instance, new therapeutic approaches that employ electrical stimulation of neural structures that directly address the underlying cardiac autonomic nervous system imbalance and dysregulation have been proposed. In one form, controlled stimulation of the cervical vagus nerve beneficially modulates cardiovascular regulatory function. Vagus nerve stimulation (VNS) has been used for the clinical treatment of drug-refractory epilepsy and depression, and more recently has been proposed as a therapeutic treatment of heart conditions such as CHF. For instance, VNS has been demonstrated in canine studies as efficacious in simulated treatment of AF and heart failure, such as described in Zhang et al., "Chronic Vagus Nerve Stimulation Improves Autonomic Control and Attenuates Systemic Inflammation and Heart Failure Progression in a Canine High-Rate Pacing Model," Circ Heart Fail 2009, 2, pp. 692-699 (Sep. 22, 2009), the disclosure of which is incorporated by reference. The results of a multi-center open-label phase II study in which chronic VNS was utilized for CHF patients with severe systolic dysfunction is described in De Ferrari et al., "Chronic Vagus Nerve Stimulation: A New and Promising Therapeutic Approach for Chronic Heart Failure," European Heart Journal, 32, pp. 847-855 (Oct. 28, 2010).

VNS therapy commonly requires implantation of a neurostimulator, a surgical procedure requiring several weeks of recovery before the neurostimulator can be activated and a patient can start receiving VNS therapy. Even after the recovery and activation of the neurostimulator, a full therapeutic dose of VNS is not immediately delivered to the patient to avoid causing significant patient discomfort and other undesirable side effects. Instead, to allow the patient to adjust to the VNS therapy, a titration process is utilized in which the intensity is gradually increased over a period of time under a control of a physician, with the patient given time between successive increases in VNS therapy intensity to adapt to the new intensity. As stimulation is chronically applied at each new intensity level, the patient's tolerance threshold, or tolerance zone boundary, gradually increases, allowing for an increase in intensity during subsequent titration sessions. The titration process can take significantly longer in practice because the increase in intensity is generally performed by a physician or other healthcare provider, and thus, for every step in the titration process to take place, the patient has to visit the provider's office to have the titration performed. Scheduling conflicts in the provider's office may increase the time between titration sessions, thereby extending the overall titration process, during which the patient in need of VNS does not receive the VNS at the full therapeutic intensity.

For patients receiving VNS therapy for the treatment of epilepsy, a titration process that continues over an extended period of time, such as six to twelve months, may be somewhat acceptable because the patient's health condition typically would not worsen in that period of time. However, for patients being treated for other health conditions, such as CHF, the patient's condition may degrade rapidly if left untreated. As a result, there is a much greater urgency to completing the VNS titration process when treating a patient with a time-sensitive condition, such as CHF.

Accordingly, a need remains for an approach to efficiently titrate neurostimulation therapy for treating chronic cardiac dysfunction and other conditions.

SUMMARY

Systems and methods are provided for delivering neurostimulation therapies to patients. A titration process is used to gradually increase the stimulation intensity to a desired therapeutic level. One or more titration parameters, such as, e.g., an acclimation interval between titration sessions, a pulse amplitude, a pulse frequency, a pulse width, and a stimulation duty cycle, may be adjusted based on the patient's response to the stimulation. This personalized titration process can minimize the amount of time required to complete titration so as to begin delivery of the stimulation at therapeutically desirable levels. The amount of time between titration sessions can be adjusted based on the patient's actual rate of VNS adaption, instead of initiating titration sessions based on a predetermined schedule. Because patients adapt to VNS stimulation at different rates, a systematic approach to titrating the stimulation parameters can provide a tailored process for each patient, thereby further reducing the total titration duration for patients who acclimate to the stimulation at a faster than average rate.

In accordance with embodiments of the present invention, a method of operating an implantable medical device (IMD) comprising a neurostimulator coupled to an electrode assembly is provided. The method comprises: initiating a plurality of titration sessions, each titration session separated from an adjacent titration session by an acclimation interval, wherein the titration sessions comprise activating the IMD to deliver a stimulation signal of gradually increasing intensity until the patient exceeds a side effect tolerance zone boundary; analyzing an outcome measure of the plurality of titration sessions; and modifying one or more stimulation parameters based on the analyzed outcome measure.

Still other embodiments of the present invention will become readily apparent to those skilled in the art from the following detailed description, wherein are described embodiments by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

CHF and other cardiovascular diseases cause derangement of autonomic control of the cardiovascular system, favoring increased sympathetic and decreased parasympathetic central outflow. These changes are accompanied by elevation of basal heart rate arising from chronic sympathetic hyperactivation along the neurocardiac axis.

The vagus nerve is a diverse nerve trunk that contains both sympathetic and parasympathetic fibers, and both afferent and efferent fibers. These fibers have different diameters and myelination, and subsequently have different activation thresholds. This results in a graded response as intensity is increased. Low intensity stimulation results in a progressively greater tachycardia, which then diminishes and is replaced with a progressively greater bradycardia response as intensity is further increased. Peripheral neurostimulation therapies that target the fluctuations of the autonomic nervous system have been shown to improve clinical outcomes in some patients. Specifically, autonomic regulation therapy results in simultaneous creation and propagation of efferent and afferent action potentials within nerve fibers comprising the cervical vagus nerve. The therapy directly improves autonomic balance by engaging both medullary and cardiovascular reflex control components of the autonomic nervous system. Upon stimulation of the cervical vagus nerve, action potentials propagate away from the stimulation site in two directions, efferently toward the heart and afferently toward the brain. Efferent action potentials influence the intrinsic cardiac nervous system and the heart and other organ systems, while afferent action potentials influence central elements of the nervous system.

Figure 1:
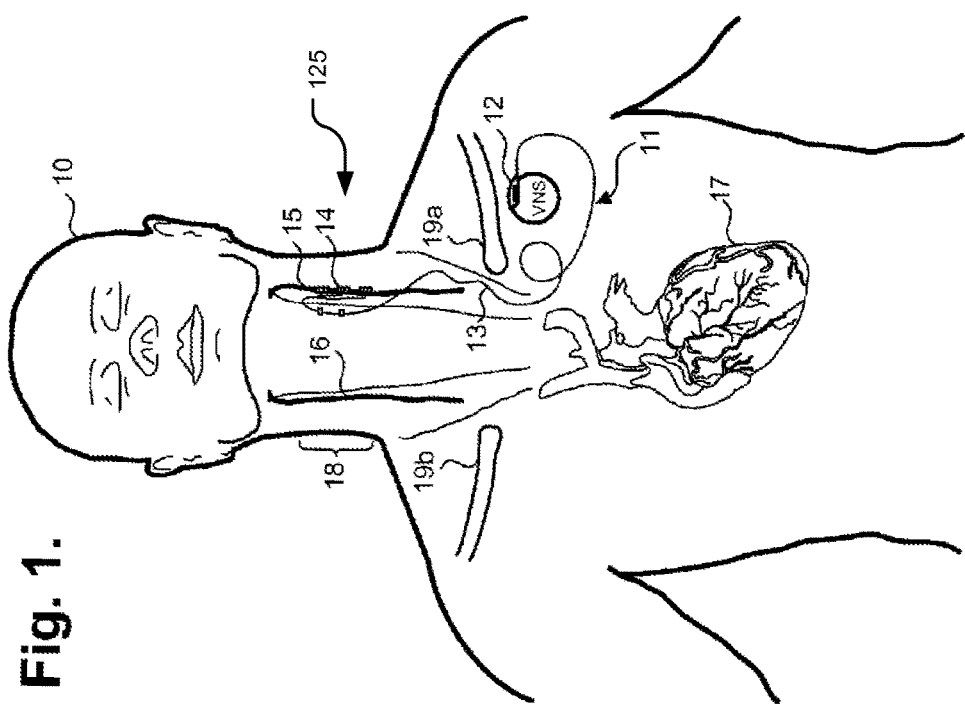
FIG. 1 is a front anatomical diagram showing, by way of example, placement of an implantable vagus stimulation device in a male patient, in accordance with one embodiment.

An implantable vagus nerve stimulator, such as used to treat drug-refractory epilepsy and depression, can be adapted for use in managing chronic cardiac dysfunction (CCD) through therapeutic bi-directional vagus nerve stimulation. FIG. 1 is a front anatomical diagram showing, by way of example, placement of an implantable medical device (e.g., a vagus nerve stimulation (VNS) system 11, as shown in FIG. 1) in a male patient 10, in accordance with embodiments of the present invention. The VNS provided through the stimulation system 11 operates under several mechanisms of action. These mechanisms include increasing parasympathetic outflow and inhibiting sympathetic effects by inhibiting norepinephrine release and adrenergic receptor activation. More importantly, VNS triggers the release of the endogenous neurotransmitter acetylcholine and other peptidergic substances into the synaptic cleft, which has several beneficial anti-arrhythmic, anti-apoptotic, and anti-inflammatory effects as well as beneficial effects at the level of the central nervous system.

The implantable vagus stimulation system 11 comprises an implantable neurostimulator or pulse generator 12 and a stimulating nerve electrode assembly 125. The stimulating nerve electrode assembly 125, preferably comprising at least an electrode pair, is conductively connected to the distal end of an insulated, electrically conductive lead assembly 13 and electrodes 14. The electrodes 14 may be provided in a variety of forms, such as, e.g., helical electrodes, probe electrodes, cuff electrodes, as well as other types of electrodes.

Figure 3:
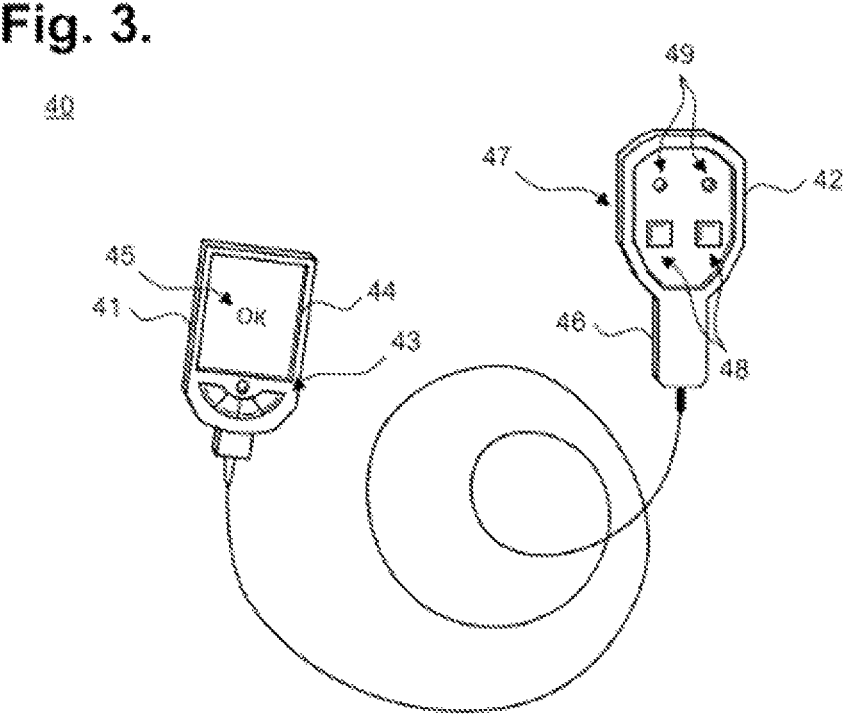
FIG. 3 is a diagram showing an external programmer for use with the implantable neurostimulator of FIG. 1.

The implantable vagus stimulation system 11 can be remotely accessed following implant through an external programmer, such as the programmer 40 shown in FIG. 3 and described in further detail below. The programmer 40 can be used by healthcare professionals to check and program the neurostimulator 12 after implantation in the patient 10 and to adjust stimulation parameters during the initial stimulation titration process. In some embodiments, an external magnet may provide basic controls, such as described in commonly assigned U.S. Pat. No. 8,600,505, entitled "Implantable Device For Facilitating Control Of Electrical Stimulation Of Cervical Vagus Nerves For Treatment Of Chronic Cardiac Dysfunction," the disclosure of which is incorporated by reference. For further example, an electromagnetic controller may enable the patient 10 or healthcare professional to interact with the implanted neurostimulator 12 to exercise increased control over therapy delivery and suspension, such as described in commonly-assigned U.S. Pat. No. 8,571,654, entitled "Vagus Nerve Neurostimulator With Multiple Patient-Selectable Modes For Treating Chronic Cardiac Dysfunction," the disclosure of which is incorporated by reference. For further example, an external programmer may communicate with the neurostimulation system 11 via other wired or wireless communication methods, such as, e.g., wireless RF transmission. Together, the implantable vagus stimulation system 11 and one or more of the external components form a VNS therapeutic delivery system.

The neurostimulator 12 is typically implanted in the patient's right or left pectoral region generally on the same side (ipsilateral) as the vagus nerve 15, 16 to be stimulated, although other neurostimulator-vagus nerve configurations, including contra-lateral and bi-lateral are possible. A vagus nerve typically comprises two branches that extend from the brain stem respectively down the left side and right side of the patient, as seen in FIG. 1. The electrodes 14 are generally implanted on the vagus nerve 15, 16 about halfway between the clavicle 19a-b and the mastoid process. The electrodes may be implanted on either the left or right side. The lead assembly 13 and electrodes 14 are implanted by first exposing the carotid sheath and chosen branch of the vagus nerve 15, 16 through a latero-cervical incision (perpendicular to the long axis of the spine) on the ipsilateral side of the patient's neck 18. The helical electrodes 14 are then placed onto the exposed nerve sheath and tethered. A subcutaneous tunnel is formed between the respective implantation sites of the neurostimulator 12 and helical electrodes 14, through which the lead assembly 13 is guided to the neurostimulator 12 and securely connected.

In one embodiment, the neural stimulation is provided as a low level maintenance dose independent of cardiac cycle. The stimulation system 11 bi-directionally stimulates either the left vagus nerve 15 or the right vagus nerve 16. However, it is contemplated that multiple electrodes 14 and multiple leads 13 could be utilized to stimulate simultaneously, alternatively or in other various combinations. Stimulation may be through multimodal application of continuously-cycling, intermittent and periodic electrical stimuli, which are parametrically defined through stored stimulation parameters and timing cycles. Both sympathetic and parasympathetic nerve fibers in the vagosympathetic complex are stimulated. A study of the relationship between cardiac autonomic nerve activity and blood pressure changes in ambulatory dogs is described in J. Hellyer et al., "Autonomic Nerve Activity and Blood Pressure in Ambulatory Dogs," Heart Rhythm, Vol. 11(2), pp. 307-313 (February 2014). Generally, cervical vagus nerve stimulation results in propagation of action potentials from the site of stimulation in a bi-directional manner. The application of bi-directional propagation in both afferent and efferent directions of action potentials within neuronal fibers comprising the cervical vagus nerve improves cardiac autonomic balance. Afferent action potentials propagate toward the parasympathetic nervous system's origin in the medulla in the nucleus ambiguus, nucleus tractus solitarius, and the dorsal motor nucleus, as well as towards the sympathetic nervous system's origin in the intermediolateral cell column of the spinal cord. Efferent action potentials propagate toward the heart 17 to activate the components of the heart's intrinsic nervous system. Either the left or right vagus nerve 15, 16 can be stimulated by the stimulation system 11. The right vagus nerve 16 has a moderately lower (approximately 30%) stimulation threshold than the left vagus nerve 15 for heart rate effects at the same stimulation frequency and pulse width.

Figure 2A:
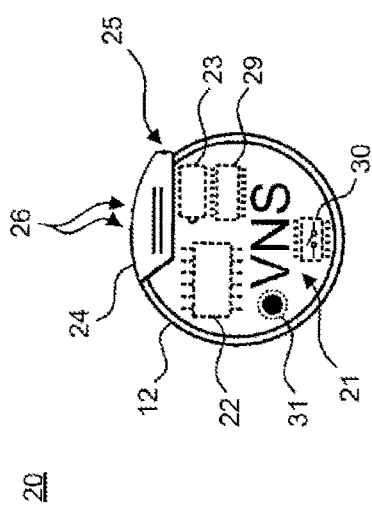
FIGS. 2A and 2B are diagrams respectively showing the implantable neurostimulator and the simulation therapy lead of FIG. 1.
Figure 2B:
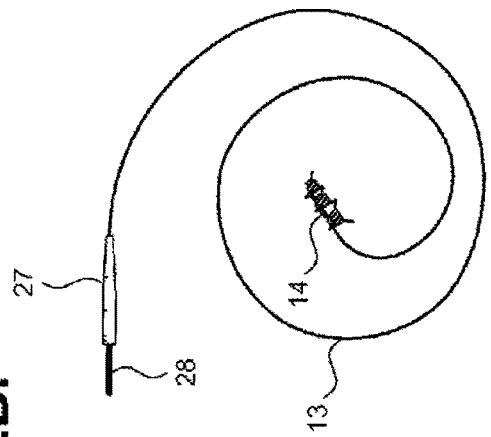

The VNS therapy is delivered autonomously to the patient's vagus nerve 15, 16 through three implanted components that include a neurostimulator 12, lead assembly 13, and electrodes 14. FIGS. 2A and 2B are diagrams respectively showing the implantable neurostimulator 12 and the stimulation lead assembly 13 of FIG. 1. In one embodiment, the neurostimulator 12 can be adapted from a VNS Therapy Demipulse Model 103 or AspireSR Model 106 pulse generator, manufactured and sold by Cyberonics, Inc., Houston, Tex., although other manufactures and types of implantable VNS neurostimulators could also be used. The stimulation lead assembly 13 and electrodes 14 are generally fabricated as a combined assembly and can be adapted from a Model 302 lead, PerenniaDURA Model 303 lead, or PerenniaFLEX Model 304 lead, also manufactured and sold by Cyberonics, Inc., in three sizes based, for example, on a helical electrode inner diameter, although other manufactures and types of single-pin receptacle-compatible therapy leads and electrodes could also be used.

Referring first to FIG. 2A, the system 20 may be configured to provide multimodal vagus nerve stimulation. In a maintenance mode, the neurostimulator 12 is parametrically programmed to deliver continuously-cycling, intermittent and periodic ON-OFF cycles of VNS. Such delivery produces action potentials in the underlying nerves that propagate bi-directionally, both afferently and efferently.

The neurostimulator 12 includes an electrical pulse generator that is tuned to improve autonomic regulatory function by triggering action potentials that propagate both afferently and efferently within the vagus nerve 15, 16. The neurostimulator 12 is enclosed in a hermetically sealed housing 21 constructed of a biocompatible material, such as titanium. The housing 21 contains electronic circuitry 22 powered by a battery 23, such as a lithium carbon monofluoride primary battery or a rechargeable secondary cell battery. The electronic circuitry 22 may be implemented using complementary metal oxide semiconductor integrated circuits that include a microprocessor controller that executes a control program according to stored stimulation parameters and timing cycles; a voltage regulator that regulates system power; logic and control circuitry, including a recordable memory 29 within which the stimulation parameters are stored, that controls overall pulse generator function, receives and implements programming commands from the external programmer, or other external source, collects and stores telemetry information, processes sensory input, and controls scheduled and sensory-based therapy outputs; a transceiver that remotely communicates with the external programmer using radio frequency signals; an antenna, which receives programming instructions and transmits the telemetry information to the external programmer; and a reed switch 30 that provides remote access to the operation of the neurostimulator 12 using an external programmer, a simple patient magnet, or an electromagnetic controller. The recordable memory 29 can include both volatile (dynamic) and non-volatile/persistent (static) forms of memory, within which the stimulation parameters and timing cycles can be stored. Other electronic circuitry and components are possible.

The neurostimulator 12 includes a header 24 to securely receive and connect to the lead assembly 13. In one embodiment, the header 24 encloses a receptacle 25 into which a single pin for the lead assembly 13 can be received, although two or more receptacles could also be provided, along with the corresponding electronic circuitry 22. The header 24 internally includes a lead connector block (not shown), a setscrew, and a spring contact (not shown) that electrically connects to the lead ring, thus completing the electrical circuit 26.

In some embodiments, the housing 21 may also contain a heart rate sensor 31 that is electrically interfaced with the logic and control circuitry, which receives the patient's sensed heart rate as sensory inputs. The heart rate sensor 31 monitors heart rate using an ECG-type electrode. Through the electrode, the patient's heart beat can be sensed by detecting ventricular depolarization. In a further embodiment, a plurality of electrodes can be used to sense voltage differentials between electrode pairs, which can undergo signal processing for cardiac physiological measures, for instance, detection of the P-wave, QRS complex, and T-wave. The heart rate sensor 31 provides the sensed heart rate to the control and logic circuitry as sensory inputs that can be used to determine the onset or presence of arrhythmias, particularly VT, and/or to monitor and record changes in the patient's heart rate over time or in response to applied stimulation signals.

Referring next to FIG. 2B, the lead assembly 13 delivers an electrical signal from the neurostimulator 12 to the vagus nerve 15, 16 via the electrodes 14. On a proximal end, the lead assembly 13 has a lead connector 27 that transitions an insulated electrical lead body to a metal connector pin 28 and metal connector ring. During implantation, the connector pin 28 is guided through the receptacle 25 into the header 24 and securely fastened in place using the setscrew 26 to electrically couple one electrode of the lead assembly 13 to the neurostimulator 12 while the spring contact makes electrical contact to the ring connected to the other electrode. On a distal end, the lead assembly 13 terminates with the electrode 14, which bifurcates into a pair of anodic and cathodic electrodes 62 (as further described infra with reference to FIG. 4). In one embodiment, the lead connector 27 is manufactured using silicone and the connector pin 28 and ring are made of stainless steel, although other suitable materials could be used, as well. The insulated lead body 13 utilizes a silicone-insulated alloy conductor material.

In some embodiments, the electrodes 14 are helical and placed around the cervical vagus nerve 15, 16 at the location below where the superior and inferior cardiac branches separate from the cervical vagus nerve. In alternative embodiments, the helical electrodes may be placed at a location above where one or both of the superior and inferior cardiac branches separate from the cervical vagus nerve. In one embodiment, the helical electrodes 14 are positioned around the patient's vagus nerve oriented with the end of the helical electrodes 14 facing the patient's head. In an alternate embodiment, the helical electrodes 14 are positioned around the patient's vagus nerve 15, 16 oriented with the end of the helical electrodes 14 facing the patient's heart 17. At the distal end, the insulated electrical lead body 13 is bifurcated into a pair of lead bodies that are connected to a pair of electrodes. The polarity of the electrodes could be configured into a proximal anode and a distal cathode, or a proximal cathode and a distal anode.

The neurostimulator 12 may be interrogated prior to implantation and throughout the therapeutic period with a healthcare provider-operable control system comprising an external programmer and programming wand (shown in FIG. 3) for checking proper operation, downloading recorded data, diagnosing problems, and programming operational parameters, such as described in commonly-assigned U.S. Pat. Nos. 8,600,505 and 8,571,654, cited supra. FIG. 3 is a diagram showing an external programmer 40 for use with the implantable neurostimulator 12 of FIG. 1. The external programmer 40 includes a healthcare provider operable programming computer 41 and a programming wand 42. Generally, use of the external programmer is restricted to healthcare providers, while more limited manual control is provided to the patient through "magnet mode."

In one embodiment, the external programmer 40 executes application software 45 specifically designed to interrogate the neurostimulator 12. The programming computer 41 interfaces to the programming wand 42 through a wired or wireless data connection. The programming wand 42 can be adapted from a Model 201 Programming Wand, manufactured and sold by Cyberonics, Inc., and the application software 45 can be adapted from the Model 250 Programming Software suite, licensed by Cyberonics, Inc. Other configurations and combinations of external programmer 40, programming wand 42 and application software 45 are possible.

The programming computer 41 can be implemented using a general purpose programmable computer and can be a personal computer, laptop computer, ultrabook computer, netbook computer, handheld computer, tablet computer, smart phone, or other form of computational device. In one embodiment, the programming computer is a tablet computer that may operate under the iOS operating system from Apple Inc., such as the iPad from Apple Inc., or may operate under the Android operating system from Google Inc., such as the Galaxy Tab from Samsung Electronics Co., Ltd. In an alternative embodiment, the programming computer is a personal digital assistant handheld computer operating under the Pocket-PC, Windows Mobile, Windows Phone, Windows RT, or Windows operating systems, licensed by Microsoft Corporation, Redmond, Wash., such as the Surface from Microsoft Corporation, the Dell Axim X5 and X50 personal data assistants, sold by Dell, Inc., Round Top, Tex., the HP Jornada personal data assistant, sold by Hewlett-Packard Company, Palo Alto, Tex. The programming computer 41 functions through those components conventionally found in such devices, including, for instance, a central processing unit, volatile and persistent memory, touch-sensitive display, control buttons, peripheral input and output ports, and network interface. The computer 41 operates under the control of the application software 45, which is executed as program code as a series of process or method modules or steps by the programmed computer hardware. Other assemblages or configurations of computer hardware, firmware, and software are possible.

Operationally, the programming computer 41, when connected to a neurostimulator 12 through wireless telemetry using the programming wand 42, can be used by a healthcare provider to remotely interrogate the neurostimulator 12 and modify stored stimulation parameters. The programming wand 42 provides data conversion between the digital data accepted by and output from the programming computer and the radio frequency signal format that is required for communication with the neurostimulator 12. In other embodiments, the programming computer may communicate with the implanted neurostimulator 12 using other wireless communication methods, such as wireless RF transmission. The programming computer 41 may further be configured to receive inputs, such as physiological signals received from patient sensors (e.g., implanted or external). These sensors may be configured to monitor one or more physiological signals, e.g., vital signs, such as body temperature, pulse rate, respiration rate, blood pressure, etc. These sensors may be coupled directly to the programming computer 41 or may be coupled to another instrument or computing device which receives the sensor input and transmits the input to the programming computer 41. The programming computer 41 may monitor, record, and/or respond to the physiological signals in order to effectuate stimulation delivery in accordance with embodiments of the present invention.

The healthcare provider operates the programming computer 41 through a user interface that includes a set of input controls 43 and a visual display 44, which could be touch-sensitive, upon which to monitor progress, view downloaded telemetry and recorded physiology, and review and modify programmable stimulation parameters. The telemetry can include reports on device history that provide patient identifier, implant date, model number, serial number, magnet activations, total ON time, total operating time, manufacturing date, and device settings and stimulation statistics and on device diagnostics that include patient identifier, model identifier, serial number, firmware build number, implant date, communication status, output current status, measured current delivered, lead impedance, and battery status. Other kinds of telemetry or telemetry reports are possible.

During interrogation, the programming wand 42 is held by its handle 46 and the bottom surface 47 of the programming wand 42 is placed on the patient's chest over the location of the implanted neurostimulator 12. A set of indicator lights 49 can assist with proper positioning of the wand and a set of input controls 48 enable the programming wand 42 to be operated directly, rather than requiring the healthcare provider to awkwardly coordinate physical wand manipulation with control inputs via the programming computer 41. The sending of programming instructions and receipt of telemetry information occur wirelessly through radio frequency signal interfacing. Other programming computer and programming wand operations are possible.

Figure 4:
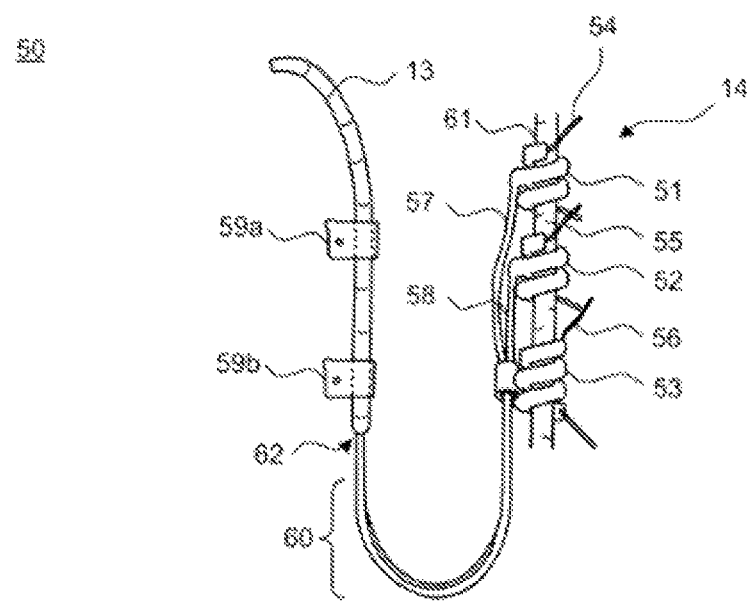
FIG. 4 is a diagram showing electrodes provided as on the stimulation therapy lead of FIG. 2 in place on a vagus nerve in situ.

FIG. 4 is a diagram showing the helical electrodes 14 provided as on the stimulation lead assembly 13 of FIG. 2 in place on a vagus nerve 15, 16 in situ 50. Although described with reference to a specific manner and orientation of implantation, the specific surgical approach and implantation site selection particulars may vary, depending upon physician discretion and patient physical structure.

Under one embodiment, helical electrodes 14 may be positioned on the patient's vagus nerve 61 oriented with the end of the helical electrodes 14 facing the patient's head. At the distal end, the insulated electrical lead body 13 is bifurcated into a pair of lead bodies 57, 58 that are connected to a pair of electrodes 51, 52. The polarity of the electrodes 51, 52 could be configured into a proximal anode and a distal cathode, or a proximal cathode and a distal anode. In addition, an anchor tether 53 is fastened over the lead bodies 57, 58 that maintains the helical electrodes' position on the vagus nerve 61 following implant. In one embodiment, the conductors of the electrodes 51, 52 are manufactured using a platinum and iridium alloy, while the helical materials of the electrodes 51, 52 and the anchor tether 53 are a silicone elastomer.

During surgery, the electrodes 51, 52 and the anchor tether 53 are coiled around the vagus nerve 61 proximal to the patient's head, each with the assistance of a pair of sutures 54, 55, 56, made of polyester or other suitable material, which help the surgeon to spread apart the respective helices. The lead bodies 57, 58 of the electrodes 51, 52 are oriented distal to the patient's head and aligned parallel to each other and to the vagus nerve 61. A strain relief bend 60 can be formed on the distal end with the insulated electrical lead body 13 aligned, for example, parallel to the helical electrodes 14 and attached to the adjacent fascia by a plurality of tie-downs 59a-b.

The neurostimulator 12 delivers VNS under control of the electronic circuitry 22. The stored stimulation parameters are programmable. Each stimulation parameter can be independently programmed to define the characteristics of the cycles of therapeutic stimulation and inhibition to ensure optimal stimulation for a patient 10. The programmable stimulation parameters include output current, signal frequency, pulse width, signal ON time, signal OFF time, magnet activation (for VNS specifically triggered by "magnet mode"), and reset parameters. Other programmable parameters are possible. In addition, sets or "profiles" of preselected stimulation parameters can be provided to physicians with the external programmer and fine-tuned to a patient's physiological requirements prior to being programmed into the neurostimulator 12, such as described in commonly-assigned U.S. Pat. No. 8,630,709, entitled "Computer-Implemented System and Method for Selecting Therapy Profiles of Electrical Stimulation of Cervical Vagus Nerves for Treatment of Chronic Cardiac Dysfunction," the disclosure of which is incorporated by reference.

Therapeutically, the VNS may be delivered as a multimodal set of therapeutic doses, which are system output behaviors that are pre-specified within the neurostimulator 12 through the stored stimulation parameters and timing cycles implemented in firmware and executed by the microprocessor controller. The therapeutic doses include a maintenance dose that includes continuously-cycling, intermittent and periodic cycles of electrical stimulation during periods in which the pulse amplitude is greater than 0 mA ("therapy ON") and during periods in which the pulse amplitude is 0 mA ("therapy OFF").

The neurostimulator 12 can operate either with or without an integrated heart rate sensor, such as respectively described in commonly-assigned U.S. Pat. No. 8,577,458, entitled "Implantable Device for Providing Electrical Stimulation of Cervical Vagus Nerves for Treatment of Chronic Cardiac Dysfunction with Leadless Heart Rate Monitoring," and U.S. patent application, entitled "Implantable Device for Providing Electrical Stimulation of Cervical Vagus Nerves for Treatment of Chronic Cardiac Dysfunction," Ser. No. 13/314,119, filed on Dec. 7, 2011, pending, the disclosures of which are hereby incorporated by reference herein in their entirety. Additionally, where an integrated leadless heart rate monitor is available, the neurostimulator 12 can provide autonomic cardiovascular drive evaluation and self-controlled titration, such as respectively described in commonly-assigned U.S. patent application entitled "Implantable Device for Evaluating Autonomic Cardiovascular Drive in a Patient Suffering from Chronic Cardiac Dysfunction," Ser. No. 13/314,133, filed on Dec. 7, 2011, U.S. Patent Publication No. 2013-0158616 A1, pending, and U.S. patent application entitled "Implantable Device for Providing Electrical Stimulation of Cervical Vagus Nerves for Treatment of Chronic Cardiac Dysfunction with Bounded Titration," Ser. No. 13/314,135, filed on Dec. 7, 2011, U.S. Patent Publication No. 2013-0158617 A1, pending, the disclosures of which are incorporated by reference. Finally, the neurostimulator 12 can be used to counter natural circadian sympathetic surge upon awakening and manage the risk of cardiac arrhythmias during or attendant to sleep, particularly sleep apneic episodes, such as respectively described in commonly-assigned U.S. patent application entitled "Implantable Neurostimulator-Implemented Method For Enhancing Heart Failure Patient Awakening Through Vagus Nerve Stimulation," Ser. No. 13/673,811, filed on Nov. 9, 2012, U.S. Patent Publication No. 2014-0135864-A1, pending, the disclosure of which is incorporated by reference.

The VNS stimulation signal may be delivered as a therapy in a maintenance dose having an intensity that is insufficient to elicit undesirable side effects, such as cardiac arrhythmias. The VNS can be delivered with a periodic duty cycle in the range of 2% to 89% with a preferred range of around 4% to 36% that is delivered as a low intensity maintenance dose. Alternatively, the low intensity maintenance dose may comprise a narrow range approximately at 17.5%, such as around 15% to 25%. The selection of duty cycle is a tradeoff among competing medical considerations. The duty cycle is determined by dividing the stimulation ON time by the sum of the ON and OFF times of the neurostimulator 12 during a single ON-OFF cycle. However, the stimulation time may also need to include ramp-up time and ramp-down time, where the stimulation frequency exceeds a minimum threshold (as further described infra with reference to FIG. 7).

Figure 5:
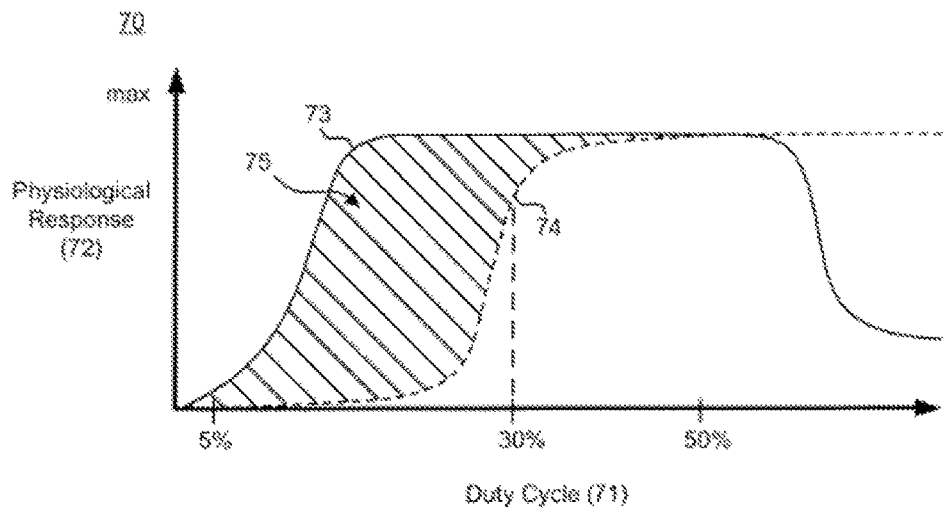
FIG. 5 is a graph showing, by way of example, the relationship between the targeted therapeutic efficacy and the extent of potential side effects resulting from use of the implantable neurostimulator of FIG. 1.

FIG. 5 is a graph 70 showing, by way of example, the relationship between the targeted therapeutic efficacy 73 and the extent of potential side effects 74 resulting from use of the implantable neurostimulator 12 of FIG. 1, after the patient has completed the titration process. The graph in FIG. 5 provides an illustration of the failure of increased stimulation intensity to provide additional therapeutic benefit, once the stimulation parameters have reached the neural fulcrum zone, as will be described in greater detail below with respect to FIG. 8. As shown in FIG. 5, the x-axis represents the duty cycle 71. The duty cycle is determined by dividing the stimulation ON time by the sum of the ON and OFF times of the neurostimulator 12 during a single ON-OFF cycle. However, the stimulation time may also include ramp-up time and ramp-down time, where the stimulation frequency exceeds a minimum threshold (as further described infra with reference to FIG. 7). When including the ramp-up and ramp-down times, the total duty cycle may be calculated as the ON time plus the ramp-up and ramp-down times divided by the OFF time, ON time, and ramp-up and ramp-down times, and may be, e.g., between 15% and 30%, and more specifically approximately 23%. The y-axis represents physiological response 72 to VNS therapy. The physiological response 72 can be expressed quantitatively for a given duty cycle 71 as a function of the targeted therapeutic efficacy 73 and the extent of potential side effects 74, as described infra. The maximum level of physiological response 72 ("max") signifies the highest point of targeted therapeutic efficacy 73 or potential side effects 74.

Targeted therapeutic efficacy 73 and the extent of potential side effects 74 can be expressed as functions of duty cycle 71 and physiological response 72. The targeted therapeutic efficacy 73 represents the intended effectiveness of VNS in provoking a beneficial physiological response for a given duty cycle and can be quantified by assigning values to the various acute and chronic factors that contribute to the physiological response 72 of the patient 10 due to the delivery of therapeutic VNS. Acute factors that contribute to the targeted therapeutic efficacy 73 include beneficial changes in heart rate variability and increased coronary flow, reduction in cardiac workload through vasodilation, and improvement in left ventricular relaxation. Chronic factors that contribute to the targeted therapeutic efficacy 73 include improved cardiovascular regulatory function, as well as decreased negative cytokine production, increased baroreflex sensitivity, increased respiratory gas exchange efficiency, favorable gene expression, renin-angiotensin-aldosterone system down-regulation, anti-arrhythmic, anti-apoptotic, and ectopy-reducing anti-inflammatory effects. These contributing factors can be combined in any manner to express the relative level of targeted therapeutic efficacy 73, including weighting particular effects more heavily than others or applying statistical or numeric functions based directly on or derived from observed physiological changes. Empirically, targeted therapeutic efficacy 73 steeply increases beginning at around a 5% duty cycle, and levels off in a plateau near the maximum level of physiological response at around a 30% duty cycle. Thereafter, targeted therapeutic efficacy 73 begins decreasing at around a 50% duty cycle and continues in a plateau near a 25% physiological response through the maximum 100% duty cycle.

Figure 6:
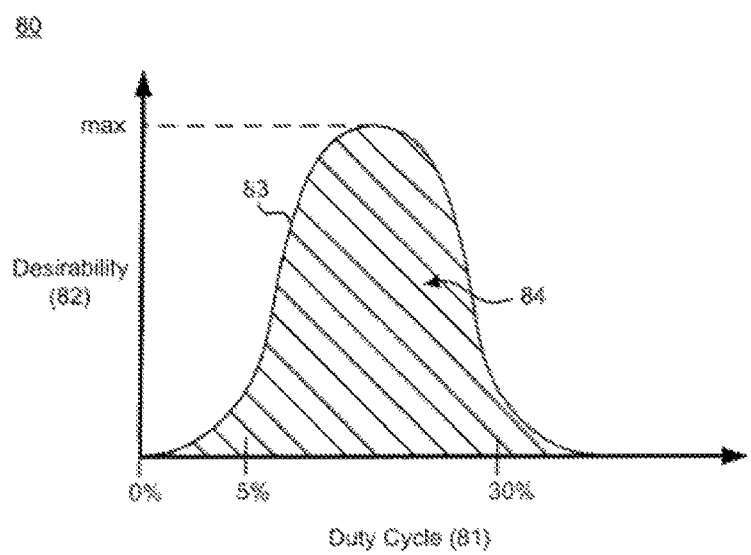
FIG. 6 is a graph showing, by way of example, the optimal duty cycle range based on the intersection depicted in FIG. 5.

The intersection 75 of the targeted therapeutic efficacy 73 and the extent of potential side effects 74 represents one optimal duty cycle range for VNS. FIG. 6 is a graph 80 showing, by way of example, the optimal duty cycle range 83 based on the intersection 75 depicted in FIG. 5. The x-axis represents the duty cycle 81 as a percentage of stimulation time over stimulation time plus inhibition time. The y-axis represents therapeutic points 82 reached in operating the neurostimulator 12 at a given duty cycle 81. The optimal duty cycle range 83 is a function 84 of the intersection 75 of the targeted therapeutic efficacy 73 and the extent of potential side effects 74. The therapeutic operating points 82 can be expressed quantitatively for a given duty cycle 81 as a function of the values of the targeted therapeutic efficacy 73 and the extent of potential side effects 74 at the given duty cycle shown in the graph 70 of FIG. 5. The optimal therapeutic operating point 85 ("max") signifies a tradeoff that occurs at the point of highest targeted therapeutic efficacy 73 in light of lowest potential side effects 74 and that point will typically be found within the range of a 5% to 30% duty cycle 81. Other expressions of duty cycles and related factors are possible.

Figure 7:
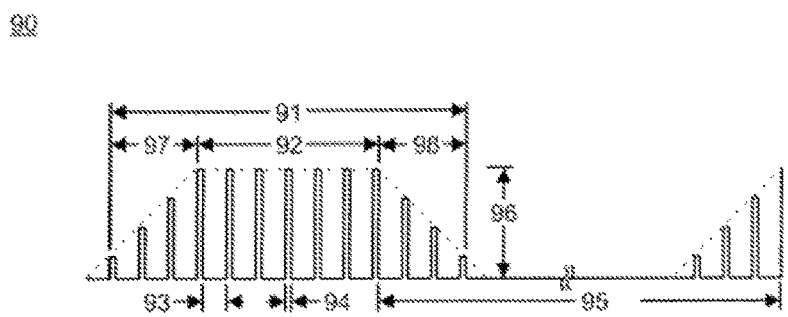
FIG. 7 is a timing diagram showing, by way of example, a stimulation cycle and an inhibition cycle of VNS as provided by implantable neurostimulator of FIG. 1.

Therapeutically and in the absence of patient physiology of possible medical concern, such as cardiac arrhythmias, VNS is delivered in a low level maintenance dose that uses alternating cycles of stimuli application (ON) and stimuli inhibition (OFF) that are tuned to activate both afferent and efferent pathways. Stimulation results in parasympathetic activation and sympathetic inhibition, both through centrally-mediated pathways and through efferent activation of preganglionic neurons and local circuit neurons. FIG. 7 is a timing diagram showing, by way of example, a stimulation cycle and an inhibition cycle of VNS 90, as provided by implantable neurostimulator 12 of FIG. 1. The stimulation parameters enable the electrical stimulation pulse output by the neurostimulator 12 to be varied by both amplitude (output current 96) and duration (pulse width 94). The number of output pulses delivered per second determines the signal frequency 93. In one embodiment, a pulse width in the range of 100 to 250 μsec delivers between 0.02 mA and 50 mA of output current at a signal frequency of about 10 Hz, although other therapeutic values could be used as appropriate. In general, the stimulation signal delivered to the patient may be defined by a stimulation parameter set comprising at least an amplitude, a frequency, a pulse width, and a duty cycle.

In one embodiment, the stimulation time is considered the time period during which the neurostimulator 12 is ON and delivering pulses of stimulation, and the OFF time is considered the time period occurring in-between stimulation times during which the neurostimulator 12 is OFF and inhibited from delivering stimulation.

In another embodiment, as shown in FIG. 7, the neurostimulator 12 implements a stimulation time 91 comprising an ON time 92, a ramp-up time 97 and a ramp-down time 98 that respectively precede and follow the ON time 92. Under this embodiment, the ON time 92 is considered to be a time during which the neurostimulator 12 is ON and delivering pulses of stimulation at the full output current 96. Under this embodiment, the OFF time 95 is considered to comprise the ramp-up time 97 and ramp-down time 98, which are used when the stimulation frequency is at least 10 Hz, although other minimum thresholds could be used, and both ramp-up and ramp-down times 97, 98 last two seconds, although other time periods could also be used. The ramp-up time 97 and ramp-down time 98 allow the strength of the output current 96 of each output pulse to be gradually increased and decreased, thereby avoiding deleterious reflex behavior due to sudden delivery or inhibition of stimulation at a programmed intensity.

Therapeutic vagus neural stimulation has been shown to provide cardioprotective effects. Although delivered in a maintenance dose having an intensity that is insufficient to elicit undesirable side effects, such as cardiac arrhythmias, ataxia, coughing, hoarseness, throat irritation, voice alteration, or dyspnea, therapeutic VNS can nevertheless potentially ameliorate pathological tachyarrhythmias in some patients. Although VNS has been shown to decrease defibrillation threshold, VNS has not been shown to terminate VF in the absence of defibrillation. VNS prolongs ventricular action potential duration, so may be effective in terminating VT. In addition, the effect of VNS on the AV node may be beneficial in patients with AF by slowing conduction to the ventricles and controlling ventricular rate.

Neural Fulcrum Zone

As described above, autonomic regulation therapy results in simultaneous creation of action potentials that simultaneously propagate away from the stimulation site in afferent and efferent directions within axons comprising the cervical vagus nerve complex. Upon stimulation of the cervical vagus nerve, action potentials propagate away from the stimulation site in two directions, efferently toward the heart and afferently toward the brain. Different parameter settings for the neurostimulator 12 may be adjusted to deliver varying stimulation intensities to the patient. The various stimulation parameter settings for current VNS devices include output current amplitude, signal frequency, pulse width, signal ON time, and signal OFF time.

When delivering neurostimulation therapies to patients, it is generally desirable to avoid stimulation intensities that result in either excessive tachycardia or excessive bradycardia. However, researchers have typically utilized the patient's heart rate changes as a functional response indicator or surrogate for effective recruitment of nerve fibers and engagement of the autonomic nervous system elements responsible for regulation of heart rate, which may be indicative of therapeutic levels of VNS. Some researchers have proposed that heart rate reduction caused by VNS stimulation is itself beneficial to the patient.

In accordance with some embodiments, a neural fulcrum zone is identified, and neurostimulation therapy is delivered within the neural fulcrum zone. This neural fulcrum zone corresponds to a combination of stimulation parameters at which autonomic engagement is achieved but for which a functional response determined by heart rate change is nullified due to the competing effects of afferently and efferently-transmitted action potentials. In this way, the tachycardia-inducing stimulation effects are offset by the bradycardia-inducing effects, thereby minimizing side effects such as significant heart rate changes while providing a therapeutic level of stimulation. One method of identifying the neural fulcrum zone is by delivering a plurality of stimulation signals at a fixed frequency but with one or more other parameter settings changed so as to gradually increase the intensity of the stimulation.

Figure 8A:
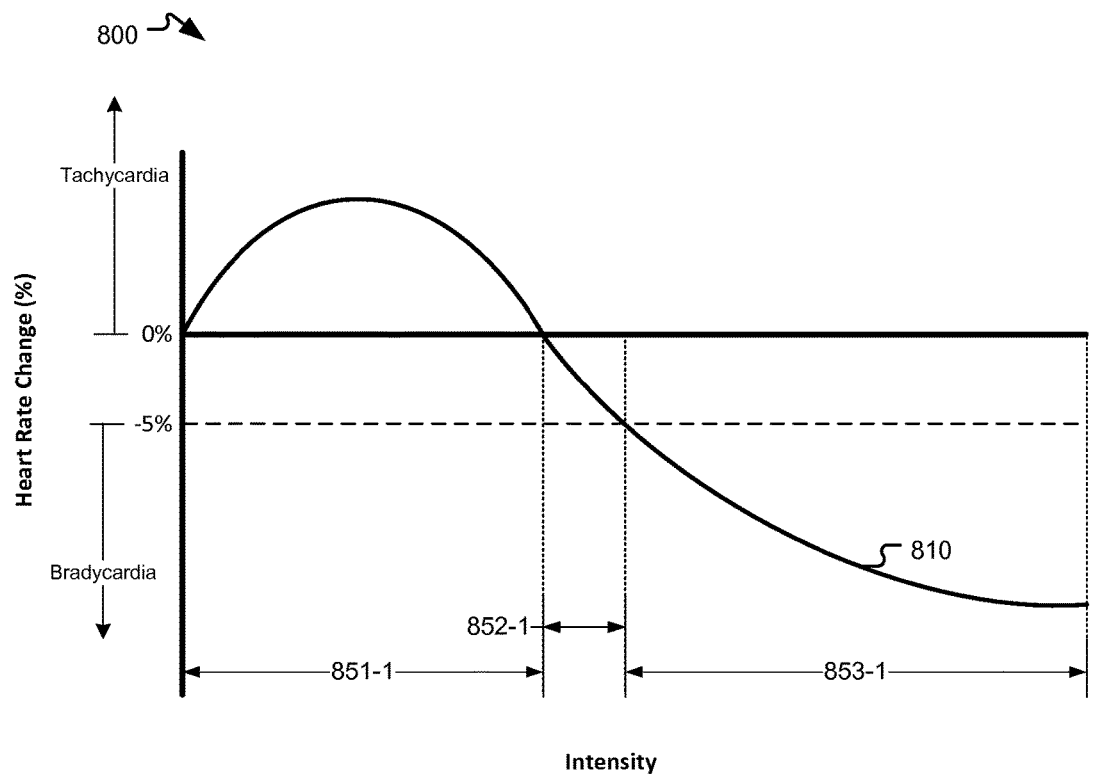
FIGS. 8A-8C are illustrative charts reflecting a heart rate response to gradually increased stimulation intensity at different frequencies.
Figure 8B:
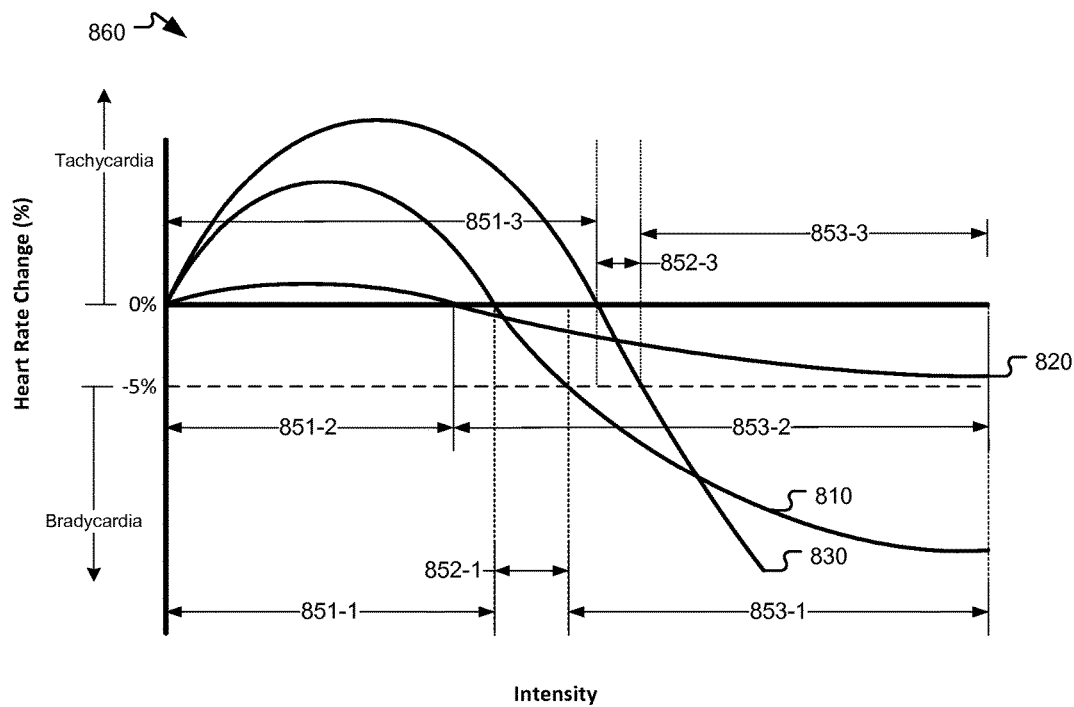
Figure 8C:
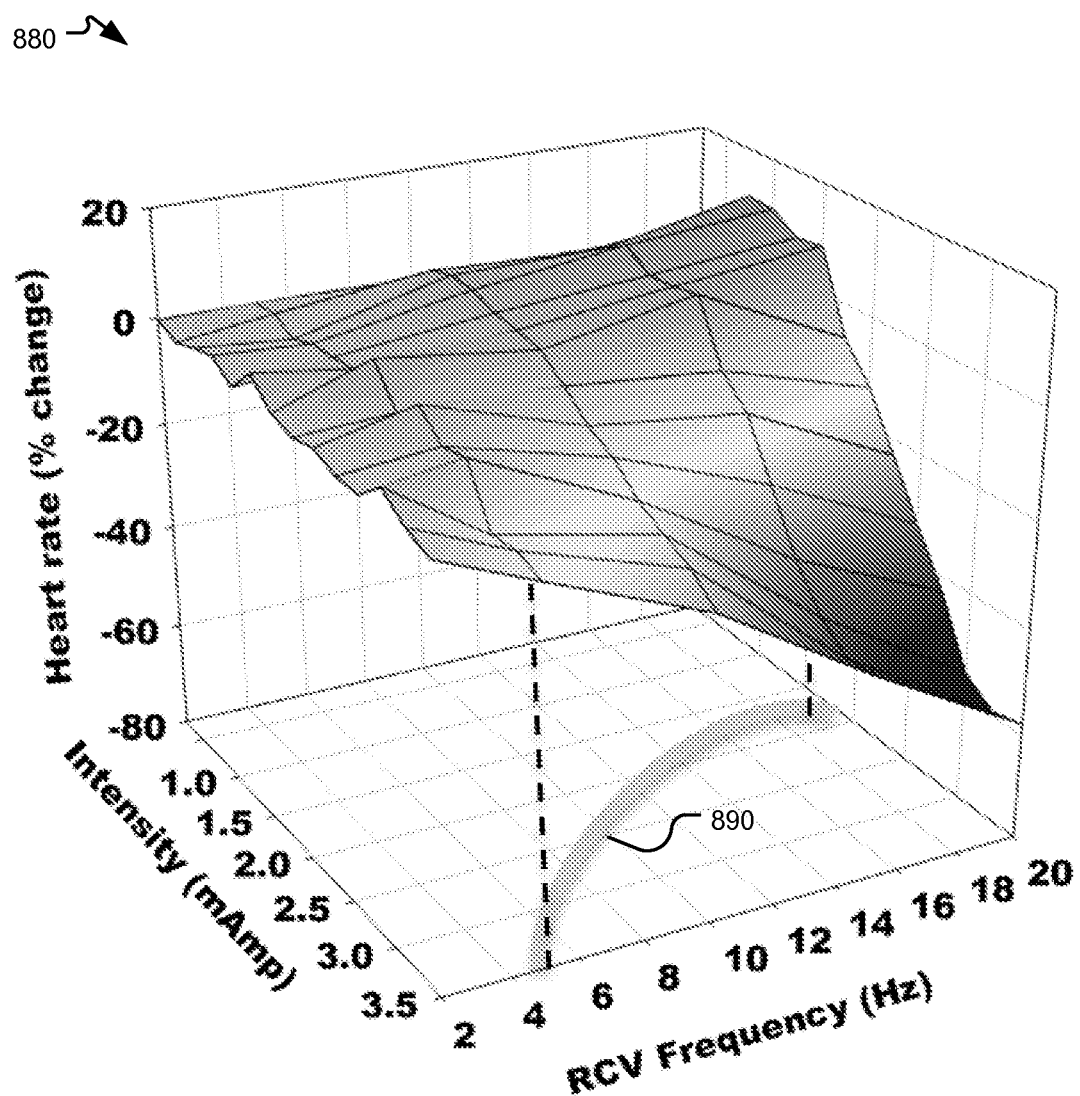

FIGS. 8A-8C provide illustrative charts reflecting the location of the neural fulcrum zone. FIG. 8A is a chart 800 illustrating a heart rate response in response to such a gradually increased intensity at a first frequency, in accordance with embodiments of the present invention. In this chart 800, the x-axis represents the intensity level of the stimulation signal, and the y-axis represents the observed heart rate change from the patient's baseline basal heart rate observed when no stimulation is delivered. In this example, the stimulation intensity is increased by increasing the output current amplitude.

A first set 810 of stimulation signals is delivered at a first frequency (e.g., 10 Hz). Initially, as the intensity (e.g., output current amplitude) is increased, a tachycardia zone 851-1 is observed, during which period, the patient experiences a mild tachycardia. As the intensity continues to be increased for subsequent stimulation signals, the patient's heart rate response begins to decrease and eventually enters a bradycardia zone 853-1, in which a bradycardia response is observed in response to the stimulation signals. As described above, the neural fulcrum zone is a range of stimulation parameters at which the functional effects from afferent activation are balanced with or nullified by the functional effects from efferent activation to avoid extreme heart rate changes while providing therapeutic levels of stimulation. In accordance with some embodiments, the neural fulcrum zone 852-1 can be located by identifying the zone in which the patient's response to stimulation produces either no heart rate change or a mildly decreased heart rate change (e.g., <5% decrease, or a target number of beats per minute). As the intensity of stimulation is further increased at the fixed first frequency, the patient enters an undesirable bradycardia zone 853-1. In these embodiments, the patient's heart rate response is used as an indicator of autonomic engagement. In other embodiments, other physiological responses may be used to indicate the zone of autonomic engagement at which the propagation of efferent and afferent action potentials are balanced, the neural fulcrum zone.

FIG. 8B is a chart 860 illustrating a heart rate response in response to such a gradually increased intensity at two additional frequencies, in accordance with embodiments of the present invention. In this chart 860, the x-axis and y-axis represent the intensity level of the stimulation signal and the observed heart rate change, respectively, as in FIG. 8A, and the first set 810 of stimulation signals from FIG. 8A is also shown.

A second set 810 of stimulation signals is delivered at a second frequency lower than the first frequency (e.g., 5 Hz). Initially, as the intensity (e.g., output current amplitude) is increased, a tachycardia zone 851-2 is observed, during which period, the patient experiences a mild tachycardia. As the intensity continues to be increased for subsequent stimulation signals, the patient's heart rate response begins to decrease and eventually enters a bradycardia zone 853-2, in which a bradycardia response is observed in response to the stimulation signals. The low frequency of the stimulation signal in the second set 820 of stimulation signals limits the functional effects of nerve fiber recruitment and, as a result, the heart response remains relatively limited. Although this low frequency stimulation results in minimal side effects, the stimulation intensity is too low to result in effective recruitment of nerve fibers and engagement of the autonomic nervous system. As a result, a therapeutic level of stimulation is not delivered.

A third set of 830 of stimulation signals is delivered at a third frequency higher than the first and second frequencies (e.g., 20 Hz). As with the first set 810 and second set 820, at lower intensities, the patient first experiences a tachycardia zone 851-3. At this higher frequency, the level of increased heart rate is undesirable. As the intensity is further increased, the heart rate decreases, similar to the decrease at the first and second frequencies but at a much higher rate. The patient first enters the neural fulcrum zone 852-3 and then the undesirable bradycardia zone 853-3. Because the slope of the curve for the third set 830 is much steeper than the second set 820, the region in which the patient's heart rate response is between 0% and −5% (e.g., the neural fulcrum zone 852-3) is much narrower than the neural fulcrum zone 852-2 for the second set 820. Accordingly, when testing different operational parameter settings for a patient by increasing the output current amplitude by incremental steps, it can be more difficult to locate a programmable output current amplitude that falls within the neural fulcrum zone 852-3. When the slope of the heart rate response curve is high, the resulting heart rate may overshoot the neural fulcrum zone and create a situation in which the functional response transitions from the tachycardia zone 851-3 to the undesirable bradycardia zone 853-3 in a single step. At that point, the clinician would need to reduce the amplitude by a smaller increment or reduce the stimulation frequency in order to produce the desired heart rate response for the neural fulcrum zone 852-3.

FIG. 8C is a chart 880 illustrating mean heart rate response surfaces in conscious, normal dogs during 14 second periods of right cervical vagus VNS stimulation ON-time. The heart rate responses shown in z-axis represent the percentage heart rate change from the baseline heart rate at various sets of VNS parameters, with the pulse width the pulse width set at 250 μsec, the pulse amplitude ranging from 0 mA to 3.5 mA (provided by the x-axis) and the pulse frequency ranging from 2 Hz to 20 Hz (provided by the y-axis). Curve 890 roughly represents the range of stimulation amplitude and frequency parameters at which a null response (i.e., 0% heart rate change from baseline) is produced. This null response curve 890 is characterized by the opposition of functional responses (e.g., tachycardia and bradycardia) arising from afferent and efferent activation.

Titration Process

Several classes of implantable medical devices provide therapy using electrical current as a stimulation vehicle. When such a system stimulates certain organs or body structures like the vagus nerve, therapeutic levels of electrical stimulation are usually not well tolerated by patients without undergoing a process known as titration. Titration is a systematic method of slowly increasing, over time, stimulation parameters employed by an implanted device to deliver stimulation current until therapeutic levels become tolerated by the patient.

Figure 9:
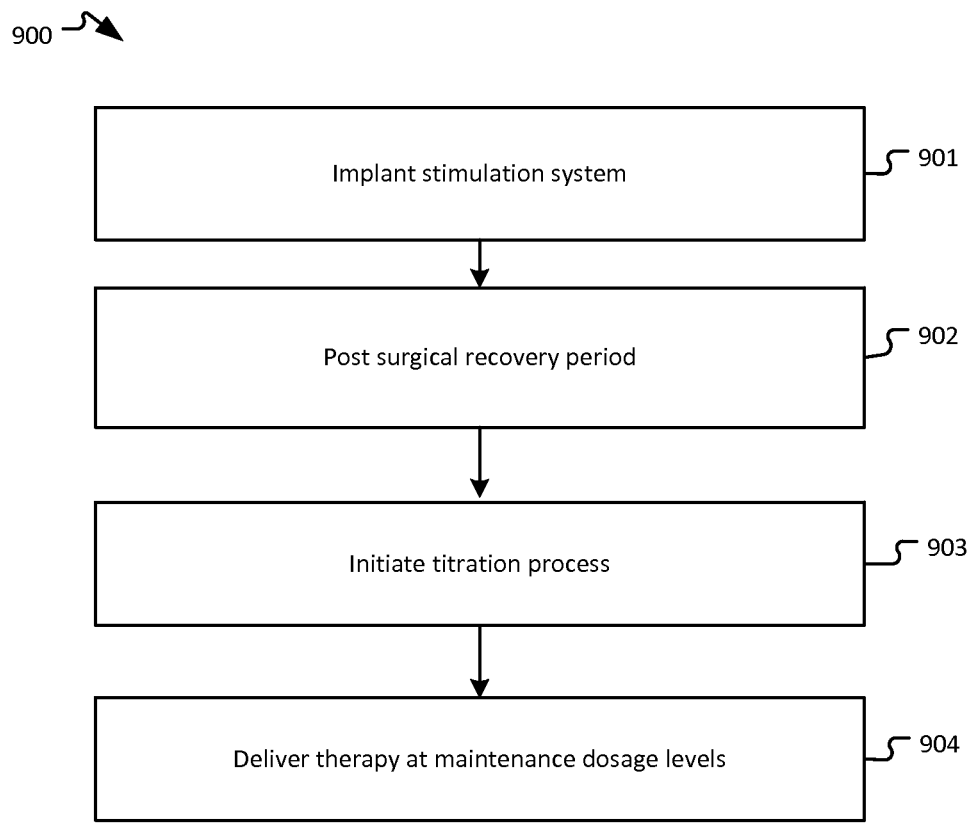
FIG. 9 illustrates a method for delivering vagus nerve stimulation therapy.

FIG. 9 is a flow diagram showing a method for delivering vagus nerve stimulation therapy, in accordance with embodiments of the present invention. A titration process is used to gradually increase the stimulation intensity to a desired therapeutic level. If the stimulation intensity is increased too quickly before the patient is fully accommodated to the stimulation signal, the patient may experience undesirable side effects, such as coughing, hoarseness, throat irritation, or expiratory reflex. The titration process gradually increases stimulation intensity within a tolerable level, and maintains that intensity for a period of time to permit the patient to adjust to each increase in intensity, thereby gradually increasing the patient's side effect tolerance zone boundary to so as to accommodate subsequent increases in intensity. The titration process continues until adequate adaptation is achieved. In embodiments, the titration process is automated and is executed by the implanted device without manual adjustment of the stimulation intensity by the subject or health care provider. As will be described in greater detail below, adequate adaptation is a composite threshold comprising one or more of the following: an acceptable side effect level, a target intensity level, and a target physiological response. In preferred embodiments, adequate adaption includes all three objectives: an acceptable side effect level, a target intensity level, and a target physiological response.

As described above, it may be desirable to minimize the amount of time required to complete the titration process so as to begin delivery of the stimulation at therapeutically desirable levels, particularly when the patient is being treated for an urgent condition such as CHF. In addition, it is desirable to utilize a maintenance dose intensity at the minimum level required to achieve the desired therapeutic effect. This can reduce power requirements for the neurostimulator and reduce patient discomfort.

It has been observed that a patient's side effect profile is more sensitive to the stimulation output current than to the other stimulation parameters, such as frequency, pulse width, and duty cycle. As a result, accommodation to the stimulation output current is a primary factor in completing the titration process. It has also been observed that if the other stimulation parameters are maintained at a level below the target levels, the output current can be increased to higher levels without eliciting undesirable side effects that would be result when the other parameters are at the target level. As a result, increasing the target output current while maintaining the other stimulation parameters (pulse width in particular) at reduced levels can result in a faster accommodation and shorter overall titration time than would be achieved by attempting to increase the output current while stimulating at the target pulse width.

In step 901, a stimulation system 11, including a neurostimulator 12, a nerve stimulation lead assembly 13, and a pair of electrodes 14, is implanted in the patient. In step 902, the patient undergoes an optional post-surgery recovery period, during which time the surgical incisions are allowed to heal and no VNS therapy occurs. This period may last, e.g., two weeks post-surgery. In step 903, the stimulation therapy process is initiated. During this process, VNS therapy is titrated by adjusting one or more of the stimulation parameters, including output current, pulse width, signal frequency, and duty cycle, as will be described in greater detail below. Completion of the titration process determines the stimulation intensity to be used for subsequent maintenance doses delivered in step 904. These maintenance doses may be selected to provide the minimum stimulation intensity necessary to provide the desired therapeutic result.

Figure 10:
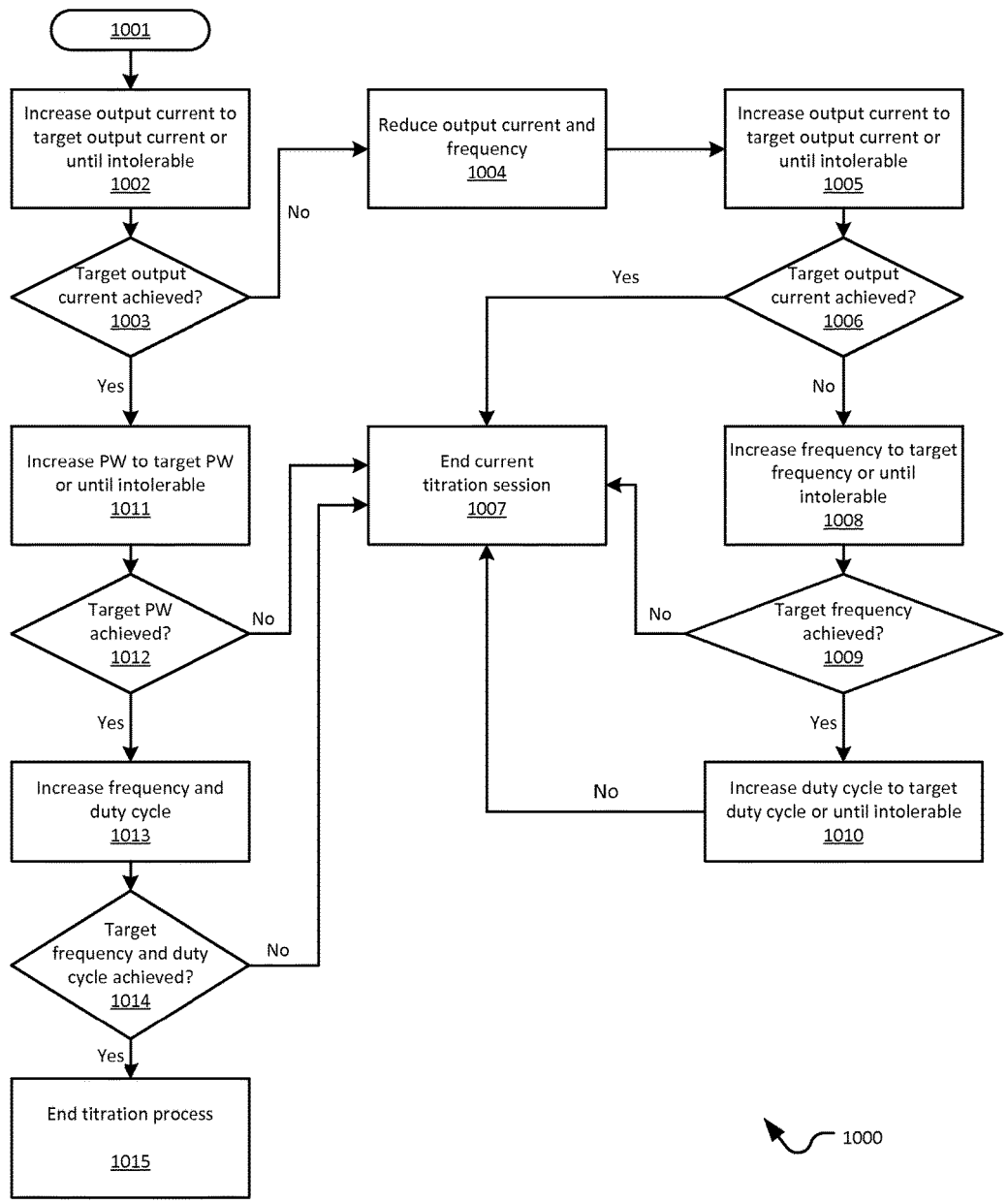
FIG. 10 illustrates a titration process in accordance with embodiments of the present invention.

FIG. 10 is a flow diagram illustrating a titration process 1000 in accordance with embodiments of the present invention. When first initiating the titration process, the neurostimulator 11 is configured to generate a stimulation signal having an initial stimulation parameter set. The initial parameter set may comprise an initial output current, an initial frequency, an initial pulse width, and an initial duty cycle. The various initial parameter settings may vary, but may be selected so that one or more of the parameters are set at levels below a predefined target parameter set level, such that the titration process is used to gradually increase the intensity parameters to achieve adequate adaptation. In some embodiments, the initial frequency is set at the target frequency level, while the initial output current, initial pulse width, and initial duty cycle are set below their respective target levels. In one embodiment, the target parameter set comprises a 10 Hz frequency, 250 μsec pulse width, a duty cycle of 14 sec ON and 1.1 minutes OFF, and an output current of between 1.5 mA-3.0 mA (e.g., 2.5 mA for right side stimulation and 3.0 mA for left side stimulation), and the initial parameter set comprises 10 Hz frequency, 130 μsec pulse width, a duty cycle of 14 sec ON and 1.1 minutes OFF, and an output current of between 0.25 mA-0.5 mA. In other embodiments, the target parameter set includes a 5 Hz frequency is used instead of a 10 Hz frequency.

In step 1001, the stimulation system delivers stimulation to the patient. If this is the first titration session, then the stimulation would be delivered with the initial stimulation parameter set described above. If this is a subsequent titration session, then the stimulation intensity would remain at the same level at the conclusion of the previous titration session.

In step 1002, the output current is gradually increased until the stimulation results in an intolerable side effect level, the target output current (e.g., 2.5 mA) is reached, or adequate adaptation is achieved. As described above, adequate adaptation is a composite threshold comprising one or more of the following: an acceptable side effect level, a target intensity level, and a target physiological response. In accordance with some embodiments, the target physiological response comprises a target heart rate change during stimulation. The patient's heart rate may be monitored using an implanted or external heart rate monitor, and the patient's heart rate during stimulation is compared to the patient's baseline heart rate to determine the extent of heart rate change. In accordance with some embodiments, the target heart rate change is a heart rate change of between 4% and 5%. If at any point during the titration process 1000 adequate adaptation is achieved, the titration process ends and the stimulation intensity which resulted in the adequate adaptation is used for ongoing maintenance dose therapy delivery.

The output current may be increased in any desired increment, but small increments, e.g., 0.1 mA or 0.25 mA, may be desirable so as to enable more precise adjustments. In some cases, the output current increments may be determined by the neurostimulator's maximum control capability. During the initial titration sessions, it is likely that the patient's side effect tolerance zone boundary will be reached well before the output current reaches the target level or adequate adaptation is achieved. At decision step 1003, if the target output current has not been achieved but the maximum tolerable side effects have been exceeded, the process proceeds to step 1004.

In step 1004, the output current is reduced one increment to bring the side effects within acceptable levels. In addition, the frequency is reduced. In embodiments in which the initial frequency was 10 Hz, in step 1004, the frequency may be reduced, e.g., to 5 Hz or 2 Hz.

Next, in step 1005, the output current is gradually increased again at the reduced frequency level until the stimulation results in an intolerable side effect level or the target output current (e.g., 2.5 mA) is reached. At decision step 1006, if the target output current has not been reached but the maximum tolerable side effects have been exceeded, the process proceeds to step 1007.

In step 1007, the titration session is concluded. The stimulation system may be programmed to continue delivering the stimulation signal at the last parameter settings achieved prior to conclusion of the titration session. After a period of time, another titration session may be initiated and the process returns to step 1001. This can be any period of time sufficient to permit the patient to adjust to the increased stimulation levels. This can be, for example, as little as approximately two or three days, approximately one to two weeks, approximately four to eight weeks, or any other desired period of time.

In some embodiments, the titration sessions are automatically initiated by the stimulation system or initiated by the patient without requiring any intervention by the health care provider. This can eliminate the need for the patient to schedule a subsequent visit to the health care provider, thereby potentially reducing the total amount of time needed for the titration process to complete. In these embodiments, the stimulation system may include a physiological monitor, e.g., an implanted heart rate sensor, that communicates with the stimulation system's control system to enable the control system to detect the patient's physiological response to the titration and automatically make adjustments to the titration processes described herein with reduced or no inputs from the patient or health care provider. The monitored signals can also enable the control system to detect when the target physiological response has been achieved and conclude the titration process. The stimulation system could in addition or alternatively include a patient control input to permit the patient to communicate to the control system that the acceptable side effect level has been exceeded. This control input may comprise an external control magnet that the patient can swipe over the implanted neurostimulator, or other internal or external communication device that the patient can use to provide an input to the control system. In these automatically initiated titration sessions, the stimulation system may be configured to wait a period of time after completing one session before initiating the next session. This period of time may be predetermined, e.g., two or three days, or programmable.

Returning to decision step 1006, if the target output current has not been reached but the maximum tolerable side effects have been exceeded, the process proceeds to step 1008. In step 1008, the output current is reduced one increment to restore an acceptable side effect condition, and the frequency is gradually increased until the stimulation results in an intolerable side effect level or the target frequency (e.g., 10 Hz) is reached. At decision step 1009, if the target frequency has not been reached but the maximum tolerable side effects have been exceeded, the frequency is reduced to restore an acceptable side effect level and the process proceeds to step 1007. Again, in step 1007, the current titration session is concluded and the stimulation system may be programmed to continue delivering the stimulation signal at the last parameter settings achieved prior to conclusion of the titration session.

At decision step 1009, if the target frequency has been reached before the maximum tolerable side effects have been exceeded, the duty cycle is gradually increased until the stimulation results in an intolerable side effect level or the target duty cycle (e.g., 14 sec ON and 1.1 min OFF) is reached, at which point the process proceeds to step 1007 and the titration session is concluded and ongoing stimulation delivered at the last intensity eliciting acceptable side effect levels.

Returning to decision step 1003, if the target output current has been achieved before the maximum tolerable side effects are exceeded, the process proceeds to step 1011. In step 1011, the pulse width is gradually increased until the stimulation results in an intolerable side effect level or the target pulse width (e.g., 250 µsec) is reached. In some embodiments, before step 1011, the output current is reduced (e.g., by up to 50%), and the pulse width may be increased in step 1011 at that reduced output current. After the target pulse width is achieved, the output current may be restored to the target output current. In other embodiments, the output current may be reduced (or may be retained at the reduced level established prior to step 1011, as described above), and the frequency and duty cycle are gradually increased in step 1013 at that reduced output current. This reduction in output current after achieving the target output current may enable the patient to maintain tolerability with increasing pulse width, frequency, and duty cycle in subsequent titration steps.

At decision step 1012, if the target pulse width has not been achieved before the maximum tolerable side effects have been exceeded, the pulse width is reduced to restore an acceptable side effect level and the process proceeds to step 1007. Again, in step 1007, the current titration session is concluded.

If at decision step 1012, the target pulse width has been achieved before the maximum tolerable side effects have been exceeded, the process proceeds to step 1013. In step 1013, the frequency and duty cycle are increased until the stimulation results in an intolerable side effect level or the target frequency and target duty cycle are reached. The frequency and duty cycle can be increased in step 1012 simultaneously, sequentially, or on an alternating basis.

At decision step 1014, if the target frequency and target duty cycle have not been achieved before the maximum tolerable side effects have been exceeded, the pulse width and/or frequency are reduced to restore an acceptable side effect level and the process continues to step 1007 and the titration session is concluded.

At decision step 1014, if the target pulse width and target frequency have been achieved before the maximum tolerable side effects have been exceeded, all of the stimulation parameters will have reached their target levels and the titration process concludes at step 1015. The stimulation therapy may proceed with the maintenance dose at the target stimulation levels.

In some embodiments, in step 1004, instead of reducing the frequency in order to facilitate increase of the output current, the pulse width may be reduced. For example, embodiments where the target pulse width is 250 µsec, the pulse width may be reduced, e.g., to 150 µsec or less. Then, the method proceeds to step 1005, in which the output current is gradually increased again at the reduced pulse width level until the stimulation results in an intolerable side effect level or the target output current (e.g., 2.5 mA) is reached.

Therapy can also be autonomously titrated by the neurostimulator 12 in which titration progressively occurs in a self-paced, self-monitored fashion. The progression of titration sessions may occur on an autonomous schedule or may be initiated upon receipt of an input from the patient. Ordinarily, the patient 10 is expected to visit his healthcare provider to have the stimulation parameters stored by the neurostimulator 12 in the recordable memory 29 reprogrammed using an external programmer. Alternatively, the neurostimulator 12 can be programmed to automatically titrate therapy by up titrating the VNS through periodic incremental increases using titration sessions as described above. The titration process 1000 will continue until the ultimate therapeutic goal is reached.

Following the titration period, therapeutic VNS, as parametrically defined by the maintenance dose operating mode, is delivered to at least one of the vagus nerves. The stimulation system 11 delivers electrical therapeutic stimulation to the cervical vagus nerve of a patient 10 in a manner that results in creation and propagation (in both afferent and efferent directions) of action potentials within neuronal fibers of either the left or right vagus nerve independent of cardiac cycle.

In a further embodiment, the sensed heart rate data can be used to analyze therapeutic efficacy and patient condition. For instance, statistics could be determined from the sensed heart rate, either onboard by the neurostimulator 12 or by an external device, such as a programming computer following telemetric data retrieval. The sensed heart rate data statistics can include determining a minimum heart rate over a stated time period, a maximum heart rate over a stated time period, an average heart rate over a stated time period, and a variability of heart rate over a stated period, where the stated period could be a minute, hour, day, week, month, or other selected time interval. Still other uses of the heart rate sensor 31 and the sensed heart rate data are possible.

Figure 11A:
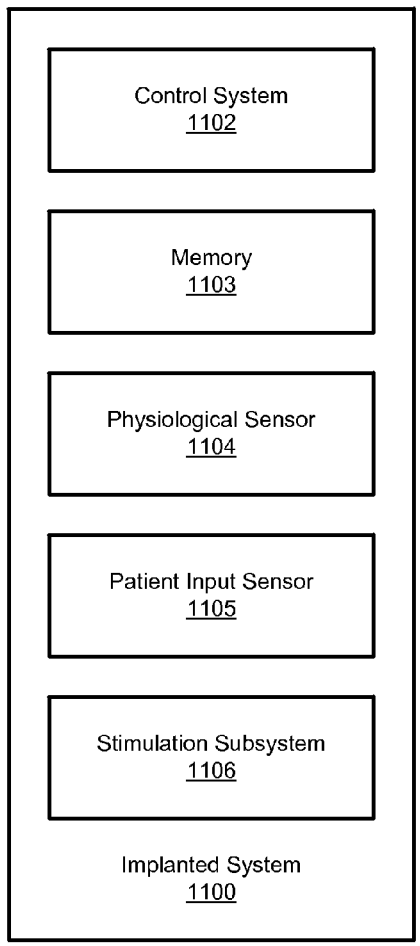
FIGS. 11A-11B are block diagrams of neurostimulation systems in accordance with embodiments of the present invention.
Figure 11A:
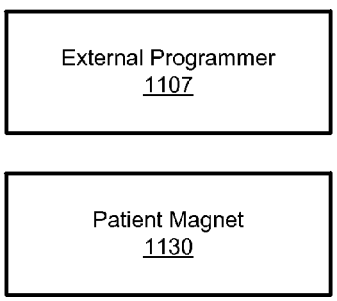

FIG. 11A is a simplified block diagram of an implanted neurostimulation system 1100 in accordance with embodiments of the present invention. The implanted neurostimulation system 1100 comprises a control system 1102 comprising a processor programmed to operate the system 1100, a memory 1103, an optional physiological sensor 1104, and a stimulation subsystem 1106. The physiological sensor 1104 may be configured to monitor any of a variety of patient physiological signals and the stimulation subsystem 1106 may be configured to deliver a stimulation signal to the patient. In one example, the physiological sensor 1104 comprises an ECG sensor for monitoring heart rate and the stimulation subsystem 1106 comprises a neurostimulator 12 programmed to deliver ON-OFF cycles of stimulation to the patient's vagus nerve.

The control system 1102 is programmed to activate the neurostimulator 12 to deliver varying stimulation intensities to the patient and to monitor the physiological signals in response to those stimulation signals.

The external programmer 1107 shown in FIG. 11A may be utilized by a clinician or by the patient for communicating with the implanted system 1100 to adjust parameters, activate therapy, retrieve data collected by the system 1100 or provide other input to the system 1100. In some embodiments, the external programmer 1107 may be configured to program the implanted system 1100 with a prescribed time or window of time during which titration sessions may be initiated. This can be used to prevent a titration session from occurring at night when the patient's sleep is likely to be disturbed by the increase in stimulation intensity and resulting side effects.

Patient inputs to the implanted system 1100 may be provided in a variety of ways. The implanted system 1100 may include a patient input sensor 1105. As described above, a patient magnet 1130 may be used to provide external input to the system 1100. When the patient magnet 1130 is placed on the patient's chest in close proximity to the implanted system 1100, the patient input sensor 1105 will detect the presence of the magnetic field generated by the patient magnet 1130 and provide a control input to the control system 1102. The system 1100 may be programmed to receive patient inputs to set the time of day during which titration sessions are to be initiated.

In other embodiments, the patient input sensor 1105 may comprise a motion sensor, such as an accelerometer, which is configured to detect tapping on the surface of the patient's chest. The patient may use finger taps in one or more predetermined patterns to provide control inputs to the implanted system 1100. For example, when the motion sensor detects three rapid taps to the patient's chest, that may trigger an operation on the implanted system 1100 (e.g., to initiate a titration session). Alternatively, if the motion sensor detects a predetermined pattern of taps during a titration session, the implanted system 1100 will interpret those taps as a patient input indicating that the patient's tolerance zone boundary has been exceeded.

In other embodiments, the patient input sensor 1105 may comprise an acoustic transducer or other sensor configured to detect acoustic signals. The system 1100 may be programmed to interpret the detection of certain sounds as patient inputs. For example, the patient may utilize an electronic device, such as a smartphone or other portable audio device, to generate one or more predetermined sequences of tones. The system 1100 may be programmed to interpret each of these sequences of tones as a different patient input.

In other embodiments, the patient input sensor 1105 may be configured to detect when a patient is coughing, which can be interpreted by the system 1100 as an indication that the increased stimulation intensity exceeds the patient's tolerance zone boundary. The coughing could be detected by an accelerometer to detect movement of the patient's chest, an acoustic transducer to detect the sound of the patient's coughing, or both.

Figure 11B:
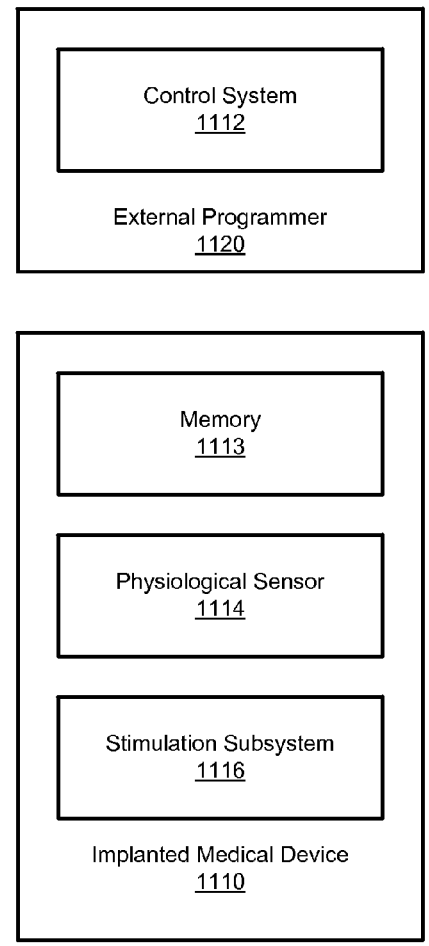

The titration of the stimulation signal delivery and the monitoring of the patient's physiological response (e.g., heart rate) may be advantageously implemented using control system in communication with both the stimulation subsystem 1106 and the physiological sensor 1104, such as by incorporating all of these components into a single implantable device. In accordance with other embodiments, the control system may be implemented in a separate implanted device or in an external programmer 1120 or other external device, as shown in FIG. 11B. The external programmer 1120 in FIG. 11B may be utilized by a clinician or by the patient for adjusting stimulation parameters. The external programmer 1120 is in wireless communication with the implanted medical device 1110, which includes the stimulation subsystem 1116. In the illustrated embodiment, the physiological sensor 1114 is incorporated into the implanted medical device 1110, but in other embodiments, the sensor 1114 may be incorporated into a separate implanted device, may be provided externally and in communication with the external programmer 1120, or may be provided as part of the external programmer 1120.

FIGS. 13-17 are flow diagrams illustrating a more detailed multi-threaded titration process 1300 that can be implemented with a stimulation system in accordance with embodiments of the present invention. Similar to titration process 1000 described above, the titration process 1300 begins at step 1301, in which the titration process is initiated and the stimulation system delivers stimulation to the patient. If this is the first titration session, then the stimulation would be delivered with an initial stimulation parameter set. If this is a subsequent titration session, then the stimulation intensity would remain at the same level at the conclusion of the previous titration session. In step 1302, an Intolerance Detection Thread 1400 (shown in FIG. 14) is initiated, and in step 1303, a Titration Execution Thread 1500 (shown in FIG. 15) is initiated. In process 1300, the two threads, 1400 and 1500, execute concurrently during the titration session. The process 1300 continues until the titration session is deemed complete in step 1304, as will be described in greater detail below. In step 1305, the Intolerance Detection Thread 1400 is terminated and in step 1306, the titration process is terminated.

Figure 14:
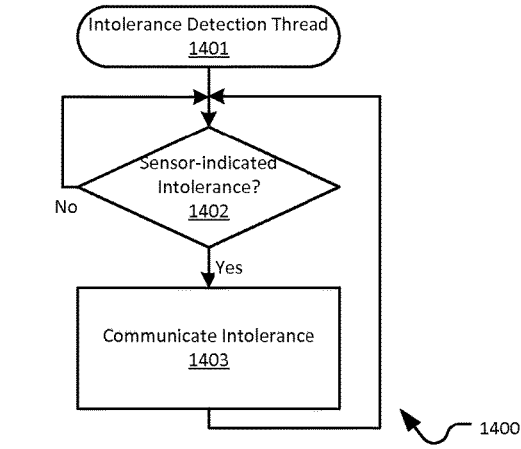

FIG. 14 is a flowchart illustrating an Intolerance Detection Thread 1400, which is a process for continuously monitoring the patient to detect stimulation intolerance in the patient. The Intolerance Detection Thread 1400 begins at step 1401, and in decision step 1402, the stimulation system continuously monitors for an indication that a side effect intolerance level has been reached. Any of the various methods for detecting intolerance described herein may be utilized for this monitoring. As long as intolerance is not detected in decision step 1402, the Intolerance Detection Thread 1400 continues monitoring for intolerance. If intolerance is detected in decision step 1402, then that intolerance is communicated in step 1403 to the subroutine currently being executed, as will be described in greater detail below.

Figure 15:
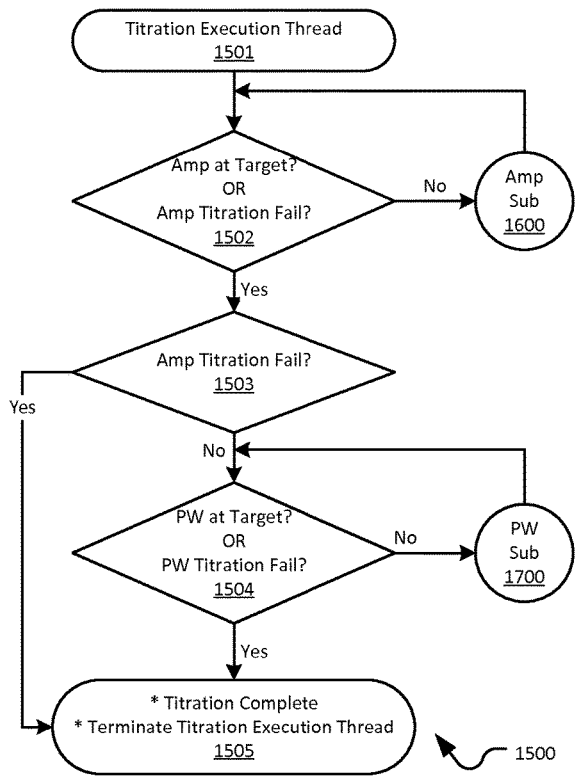

FIG. 15 is a flowchart illustrating a Titration Execution Thread 1500, which is a process for adjusting stimulation parameters during a titration session. The Titration Execution Thread 1500 begins at step 1501, decision step 1502 determines whether the stimulation amplitude is at the target level or the amplitude titration subroutine has been determined to have failed. In the initial titration session, the amplitude will be set at the initial level, which is lower than the target level, and the amplitude titration subroutine will not yet have been initiated, and will therefore not yet be determined to have failed. Accordingly, the thread 1500 will proceed to the Amplitude Subroutine 1600 (shown in FIG. 16).

If the response to either query in decision step 1502 is true, then the process 1500 will proceed to decision step 1503. In decision step 1503, if the amplitude titration subroutine has been deemed to have failed, then the process 1500 proceeds to step 1505, in which the titration session is deemed completed and the Titration Execution Thread 1500 will be terminated. If the amplitude titration subroutine has not been deemed to have failed, then the process 1500 proceeds to decision step 1504. In decision step 1504, the stimulation system determines whether the pulse width (PW) is at the target level or the pulse width titration subroutine has been determined to have failed. If the response to either query in decision step 1504 is true, then the process 1500 proceeds to step 1505, in which the titration session is deemed completed and the Titration Execution Thread 1500 will be terminated. If both queries in decision step 1504 are false, then the process 1500 proceeds to the Pulse Width Subroutine 1700 (shown in FIG. 17).

Figure 16:
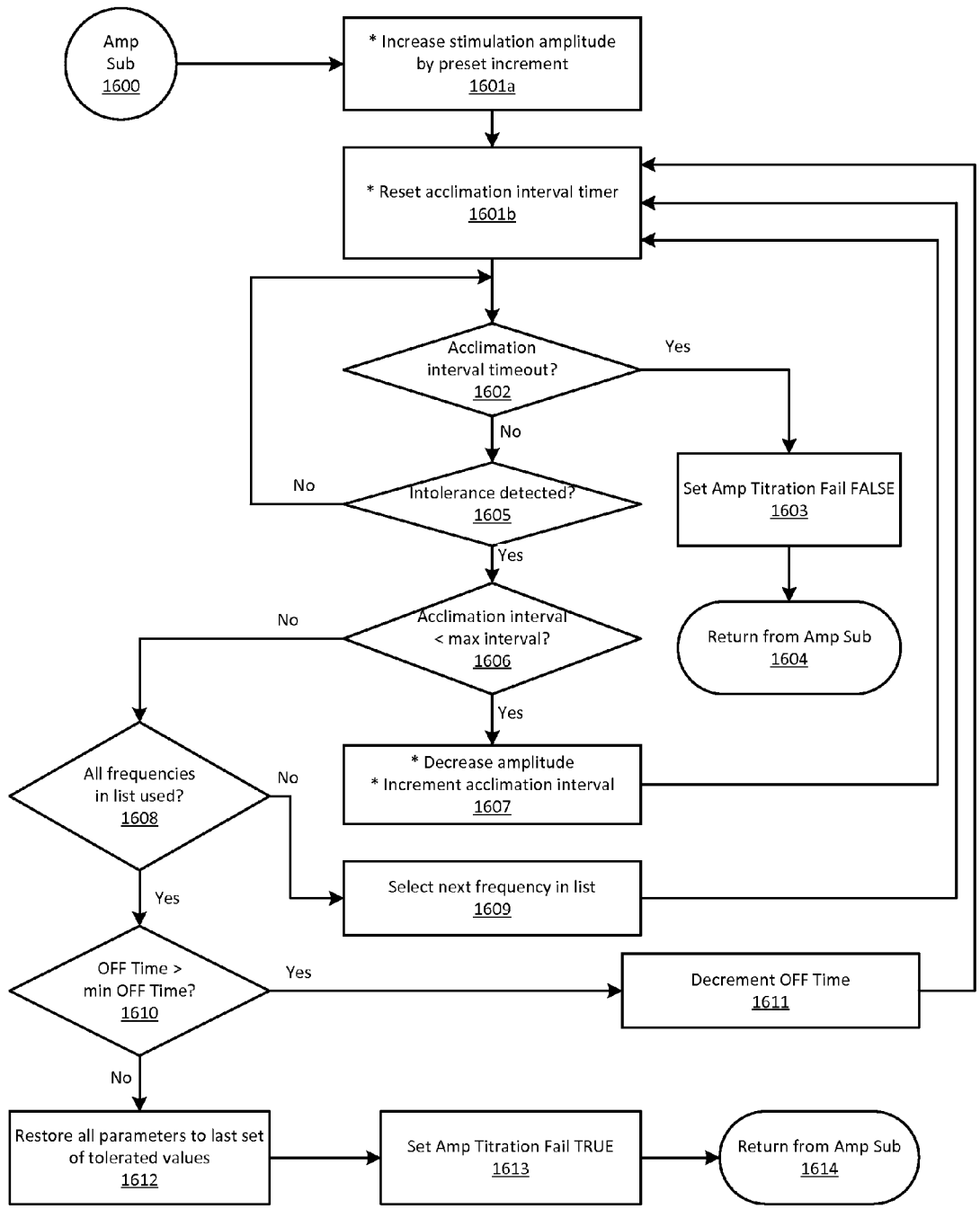

FIG. 16 is a flowchart illustrating an Amplitude Subroutine 1600, which is a more detailed process for adjusting stimulation parameters during a titration process in which an acclimation interval timeout may be increased if stimulation amplitude increases are not tolerated by the patient. The Amplitude Subroutine begins at step 1601 *a*, in which the stimulation amplitude is incrementally increased. Next, in step 1601*b*, an acclimation interval timer is reset to zero. The stimulation amplitude may be increased in any desired increment. In some embodiments, the increase is predetermined and incremented by the same amount with each increase. In other embodiments, the increases may be variable, as a function of any desired input. In some cases, the patient's responses to past increments may be used to modify the incremental increase. For example, if the patient has not experienced undesirable side effects with past increases, subsequent increases may be incremented by a larger amount. In yet other embodiments, the increments may be a function of the absolute amplitude. For example, the increments may increase in size after the amplitude has been increased beyond a certain threshold (e.g., 2.0 mA). In another example, the increments may be a percentage (e.g., 5%, 10%, or 20%) of the current stimulation amplitude. In both examples, the increments may increase as the current amplitude increases, since the patient may have a greater tolerance for amplitude increases at that point of the titration process.

The process proceeds to decision step 1602, which determines whether the acclimation interval timer indicates that an acclimation interval timeout has been reached. The acclimation interval timeout is the time interval between stimulation increases. During this acclimation interval the patient's brain becomes less sensitive to the vagus stimulation increase. The acclimation interval timeout can be a predetermined length of time, or may be variable within a titration session, as described below with respect to step 1607. The initial acclimation interval timeout could be, for example, about 2-3 days for an aggressive titration schedule, or 7-14 days for a conservative titration schedule.

If the acclimation interval timeout has not been reached (which would be the case during the initial traversal through the Amplitude Subroutine 1600), then the subroutine proceeds from decision step 1602 to decision step 1605, in which the communication regarding intolerance in step 1403 of the Intolerance Detection Thread 1400 is consulted and if intolerance is not detected, then the subroutine 1600 returns to step 1602, in which it is again determined whether the acclimation interval timeout has been reached. As a result, as long as the patient does not experience intolerable side effects, the system will maintain stimulation at the increased amplitude initiated in step 1601*a*. This ensures that the patient is provided with the full acclimation interval before the stimulation amplitude is again increased. If the acclimation interval timer indicates that the acclimation interval timeout has been reached, then the subroutine proceeds to step 1603, in which the amplitude titration subroutine will be deemed to have not failed (e.g., the Amplitude Titration Failure variable is set to FALSE), and in step 1604, the process returns to decision step 1502 in FIG. 15. This represents the success path for the titration in which the patient has tolerated the increase in stimulation amplitude. Returning to FIG. 15, the process will return to step 1502, in which the system again determines whether the stimulation amplitude is at the target level or the amplitude titration subroutine has been determined to have failed. If neither is true, then the process returns to the Amplitude Subroutine 1600, the stimulation amplitude is incrementally increased in step 1601*a*, the acclimation interval timer is reset in step 1601*b*, and the patient is again provided with a period of time to acclimate to the newly increased stimulation amplitude.

In the embodiment illustrated in FIG. 16, the acclimation interval is variable depending on the patient's response to changes in stimulation amplitude, and if an increase in amplitude in step 1601*a* is intolerable to the patient, the amplitude may be decreased and the patient is provided with an extended acclimation interval timeout at that decreased amplitude to provide the patient with an increased amount of time to acclimate to the stimulation. In this embodiment, it may be desirable to have a predetermined maximum acclimation interval, such that once the acclimation interval timeout has been increased to a level where it equals or exceeds the maximum acclimation interval, the titration process will then attempt to adjust a different stimulation parameter instead of amplitude. The maximum acclimation interval may be any period of time desired. In some embodiments, the maximum acclimation interval can be set at a multiple of the initial acclimation interval timeout, e.g., 2-5 times the initial acclimation interval timeout.

In step 1605, if the Intolerance Detection Thread 1400 has communicated that a side effect intolerance level has been reached, then the Amplitude Subroutine 1600 proceeds to decision step 1606. In decision step 1606, if the acclimation interval timeout is still less than the maximum acclimation interval, then the subroutine 1600 proceeds to step 1607. In step 1607, the amplitude is decreased by the preset increment and the acclimation interval timeout is increased by some amount, and the subroutine 1600 returns to step 1601*b*, in which the acclimation interval timer is reset to zero and stimulation is delivered at the reduced amplitude. The acclimation interval timeout may be increased by any amount, such as, for example, a predetermined period of time (e.g., 1-3 days), or by a multiple of the initial acclimation interval timeout (e.g., double the initial acclimation interval timeout).

In step 1605, if the Intolerance Detection Thread 1400 has not communicated that a side effect intolerance level has been reached, then the process will return to 1602, where subroutine will repeat in a loop and continue delivering stimulation at that amplitude until the acclimation interval timeout has been reached in step 1602 or intolerance detected in step 1605.

In decision step 1606, if the acclimation interval timeout has been increased in step 1607 to the point where it has reached the maximum acclimation interval, then the subroutine 1600 proceeds to decision step 1608, in which the system will attempt to bring the patient to the target amplitude by reducing the stimulation frequency. The stimulation system can include a predetermined list of fallback frequencies to attempt when the target amplitude cannot be tolerably achieved in a titration session. This list depends upon the starting frequency and the desired granularity for making downward adjustments. The list can be, for example, 20 Hz, 15 Hz, 10 Hz, 5 Hz, 2 Hz, and 1 Hz. If in decision step 1608 it is determined that all of the frequencies in the list of fallback frequencies have not yet been attempted during this titration session, then the subroutine 1600 proceeds to step 1609, in which the next frequency in the list is selected and stimulation applied at that new frequency. The subroutine 1600 then returns to 1601*b*, in which the acclimation interval timer is reset to zero and stimulation delivered to the patient at that new frequency. If in decision step 1608 it is determined that all of the frequencies in the list of fallback frequencies have already been attempted during this titration session, then it is concluded that the patient was not able to tolerate the stimulation even after attempting all of the reduced frequencies in the fallback frequency list, and the subroutine 1600 proceeds to decision step 1610.

In decision step 1610, if it is determined that the current stimulation OFF time is greater than a predetermined minimum OFF time, then the subroutine 1600 proceeds to step 1611, in which the stimulation OFF time is decreased by a predetermined increment. The minimum OFF time could be, for example, 10, 20, 30 seconds, or longer. The subroutine 1600 then returns to step 1601*b*, in which the acclimation interval timer is reset to zero and stimulation delivered to the patient with the decreased OFF time.

In decision step 1610, if it is determined that the current stimulation OFF time is not greater than the predetermined minimum OFF time, then the subroutine 1600 proceeds to step 1612, in which all of the stimulation parameters are restored to the last set of stimulation parameters that did not result in patient intolerance. In step 1613, the amplitude titration subroutine will be deemed to have failed (e.g., the Amplitude Titration Failure variable is set to TRUE), and in step 1614, the process returns to decision step 1502 in FIG. 15. Because the amplitude titration subroutine will be deemed to have failed, the process will proceed from decision step 1502 to decision step 1503, and then to step 1505.

After one or more titration sessions in which the Amplitude Subroutine 1600 has been performed, the target stimulation amplitude should eventually be achieved. At this point, the thread 1500 will proceed through decision steps 1502 and 1503 to decision step 1504, in which the system determines whether the stimulation pulse width is at the target level or the pulse width titration subroutine has been determined to have failed. The first time the Titration Execution Thread 1500 is executed, the pulse width will be set at a predetermined initial level, which is lower than the target PW level, and the PW titration subroutine will not yet have been initiated, and will therefore not yet be determined to have failed. Accordingly, the thread 1500 will proceed to the PW Subroutine 1700 (shown in FIG. 17).

Figure 17:
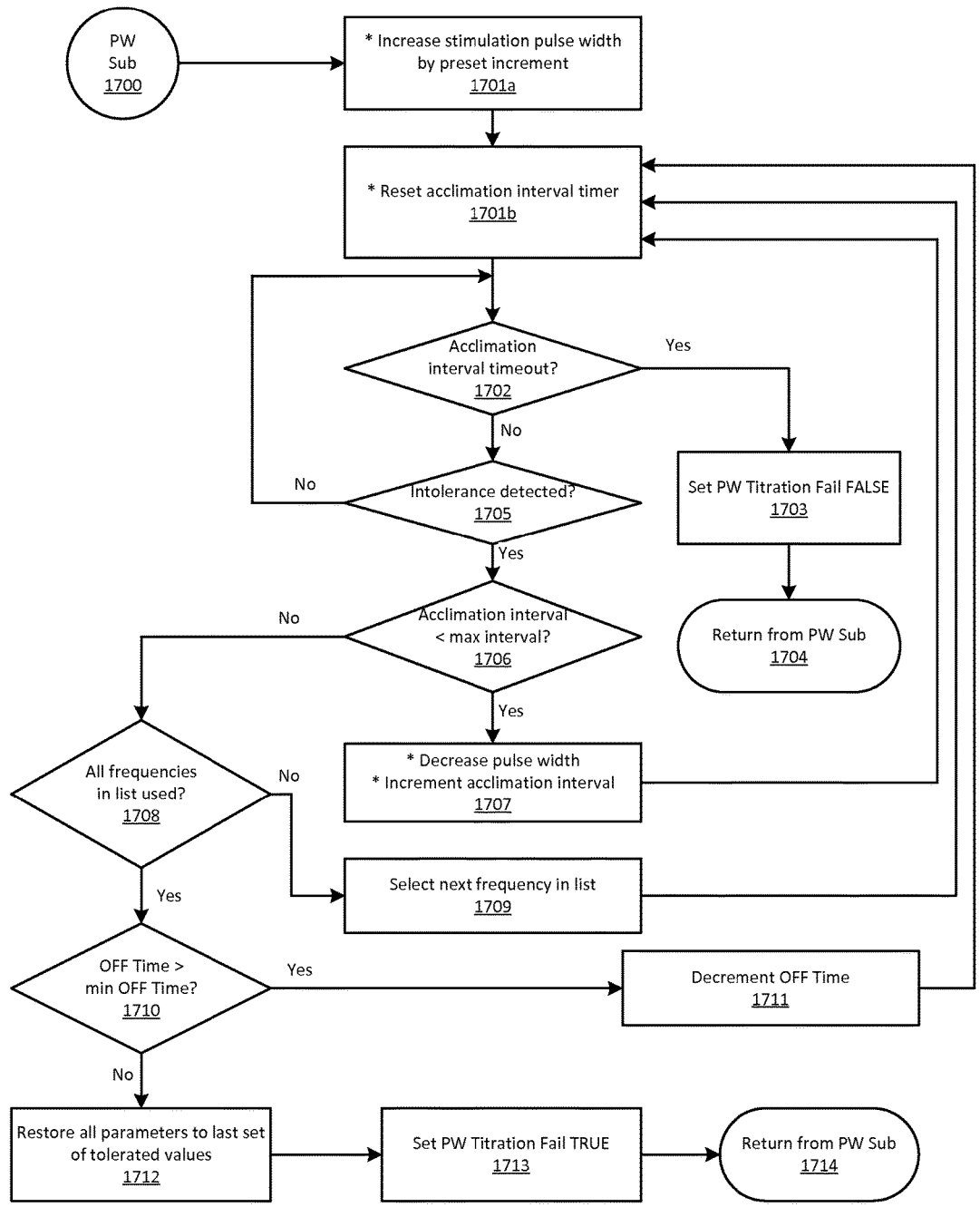

FIG. 17 is a flowchart illustrating a Pulse Width (PW) Subroutine 1700, which is similar to the Amplitude Subroutine 1600, but utilizing changes in the stimulation pulse width instead of the amplitude. The PW Subroutine begins at step 1701*a*, in which the stimulation pulse width is incrementally increased. Next, in step 1701*b*, an acclimation interval timer is reset to zero. As with the increases in amplitude in step 1601*b*, the stimulation pulse width may be increased in any desired increment. The process proceeds to decision step 1702, similar to decision step 1602, which determines whether the acclimation interval timer indicates that an acclimation interval timeout has been reached. If the acclimation interval timeout has been reached, then the subroutine proceeds to step 1703, in which the PW titration subroutine will be deemed to have not failed (e.g., the PW Titration Failure variable is set to FALSE), and in step 1704, the process returns to decision step 1504 in FIG. 15. This represents the success path for the titration in which the patient has tolerated the increase in stimulation pulse width.

If the acclimation interval timeout has not been reached, then the subroutine proceeds from step 1702 to decision step 1705, in which the communication regarding intolerance in step 1403 of the Intolerance Detection Thread 1400 is consulted and if intolerance is not detected, then the subroutine 1700 returns to step 1702, in which it is again determined whether the acclimation interval timeout has been reached. As a result, as long as the patient does not experience intolerable side effects, the system will maintain stimulation at the increased pulse width initiated in step 1701 *a*. This ensures that the patient is provided with the full acclimation interval before the stimulation pulse width is again increased. If the acclimation interval timer indicates that the acclimation interval timeout has been reached, then the subroutine proceeds to step 1703, in which the pulse width titration subroutine will be deemed to have not failed (e.g., the PW Titration Failure variable is set to FALSE), and in step 1704, the process returns to decision step 1504 in FIG. 15. This represents the success path for the titration in which the patient has tolerated the increase in stimulation pulse width. Returning to FIG. 15, the process will return to step 1504, in which the system again determines whether the stimulation pulse width is at the target level or the pulse width titration subroutine has been determined to have failed. If neither is true, then the process returns to the PW Subroutine 1700, the stimulation pulse width is incrementally increased in step 1701*a*, the acclimation interval timer is reset in step 1701*b*, and the patient is again provided with a period of time to acclimate to the newly increased stimulation pulse width.

If in step 1705, the Intolerance Detection Thread 1400 has communicated that a side effect intolerance level has been reached, then the PW Subroutine 1700 proceeds from decision step 1705 to decision step 1706. In decision step 1706, if the acclimation interval timeout is still less than the maximum acclimation interval, then the subroutine 1700 proceeds to step 1707. In step 1707, the pulse width is decreased by the preset increment and the acclimation interval timeout is increased by some amount, and the subroutine 1700 returns to step 1701*b*, in which the acclimation interval timer is reset to zero and stimulation is delivered at the reduced pulse width.

In step 1705, if the Intolerance Detection Thread 1400 has not communicated that a side effect intolerance level has been reached, then the process will return to 1702, where subroutine will repeat in a loop and continue delivering stimulation at that pulse width until the acclimation interval timeout has been reached in step 1702 or intolerance detected in step 1705.

In decision step 1706, if the acclimation interval timeout has been increased in step 1707 to the point where it has reached the maximum acclimation interval, then the subroutine 1700 proceeds to decision step 1708, in which the system will attempt to bring the patient to the target pulse width by reducing the stimulation frequency. As with subroutine 1600, the stimulation system can include a predetermined list of fallback frequencies to attempt when the target pulse width cannot be tolerably achieved in a titration session. If in decision step 1708 it is determined that all of the frequencies in the list of fallback frequencies have not yet been attempted during this titration session, then the subroutine 1700 proceeds to step 1709, in which the next frequency in the list is selected and stimulation applied at that new frequency. The subroutine 1700 then returns to 1701*b*, in which the acclimation interval timer is reset to zero and stimulation delivered to the patient at that new frequency. If in decision step 1708 it is determined that all of the frequencies in the list of fallback frequencies have already been attempted during this titration session, then it is concluded that the patient was not able to tolerate the stimulation even after attempting all of the reduced frequencies in the fallback frequency list, and the subroutine 1700 proceeds to decision step 1710.

In decision step 1710, if it is determined that the current stimulation OFF time is greater than a predetermined minimum OFF time, then the subroutine 1700 proceeds to step 1711, in which the stimulation OFF time is decreased by a predetermined increment. The predetermined minimum OFF time for the PW subroutine 1700 could be the same or different than the predetermined minimum OFF time for the amplitude subroutine 1600. The algorithm may be customizable with any desired OFF time for either the amplitude subroutine 1600 and PW subroutine 1700, depending on patient needs the desire to customize the titration for individual patients. The subroutine 1700 then returns to step 1701*b*, in which the acclimation interval timer is reset to zero and stimulation delivered to the patient with the decreased OFF time.

In decision step 1710, if it is determined that the current stimulation OFF time is not greater than the predetermined minimum OFF time, then the subroutine 1700 proceeds to step 1712, in which all of the stimulation parameters are restored to the last set of stimulation parameters that did not result in patient intolerance. In step 1713, the PW Subroutine will be deemed to have failed (e.g., the Amplitude Titration Failure variable is set to TRUE), and in step 1714, the process returns to decision step 1504 in FIG. 15. Because the amplitude titration subroutine will be deemed to have failed, the process will proceed from decision step 1504 to step 1505, at which point the titration session will be deemed complete and the titration execution thread 1500 terminated.

Figure 13:
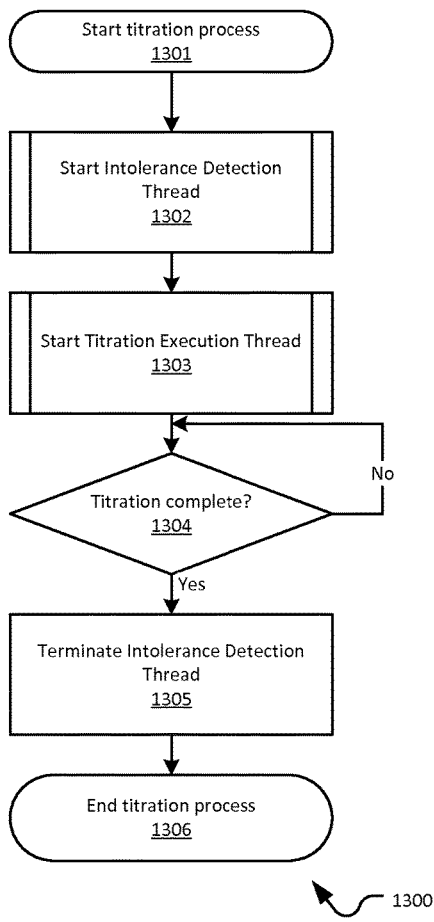
FIGS. 13-17 are flow diagrams illustrating a multi-threaded titration process in accordance with embodiments of the present invention.

Returning to the process 1300 in FIG. 13, the titration will be determined to be complete in decision step 1304, and the process 1300 will continue to step 1305, at which the intolerance detection thread 1400 will be terminated. Finally, the process 1300 will proceed to step 1306, at which point the titration session is terminated.

Personalized Titration Via Adaptive Parametric Modification

Titration is a method of varying over time stimulation parameters employed by an implanted device to deliver stimulation current, until therapeutic levels become tolerated by the patient. Embodiments provided above describe automated titration processes used to gradually increase the stimulation intensity to a desired therapeutic level. During periodic titration sessions, the stimulation intensity is increased until the maximum tolerable side effects are exceeded, at which point the stimulation intensity is reduced to a tolerable level and the patient is provided with a period of time to adapt to the new intensity levels before the next titration session is initiated. In some embodiments, the titration sessions may occur on a regular schedule (e.g., every two weeks), with an acclimation interval in between each titration session during which time stimulation at a tolerable intensity level is delivered. Then, at each titration session, the various stimulation parameters are increased by predetermined increments. However, patients adapt to increased stimulation intensity levels differently and utilizing the same acclimation intervals and other stimulation parameter incremental changes for all patients may not provide optimal results for every patient.

For example, patients adapt to increased stimulation intensity levels at different rates, so the minimum acclimation interval required before the next titration session can successfully be initiated varies. In other embodiments, parameters other than or in addition to the acclimation interval may be adjusted based on the actual adaption experienced by the patient. The parameters that might be adjusted include, for example: current amplitude, pulse width, frequency, and OFF time.

Figure 12:
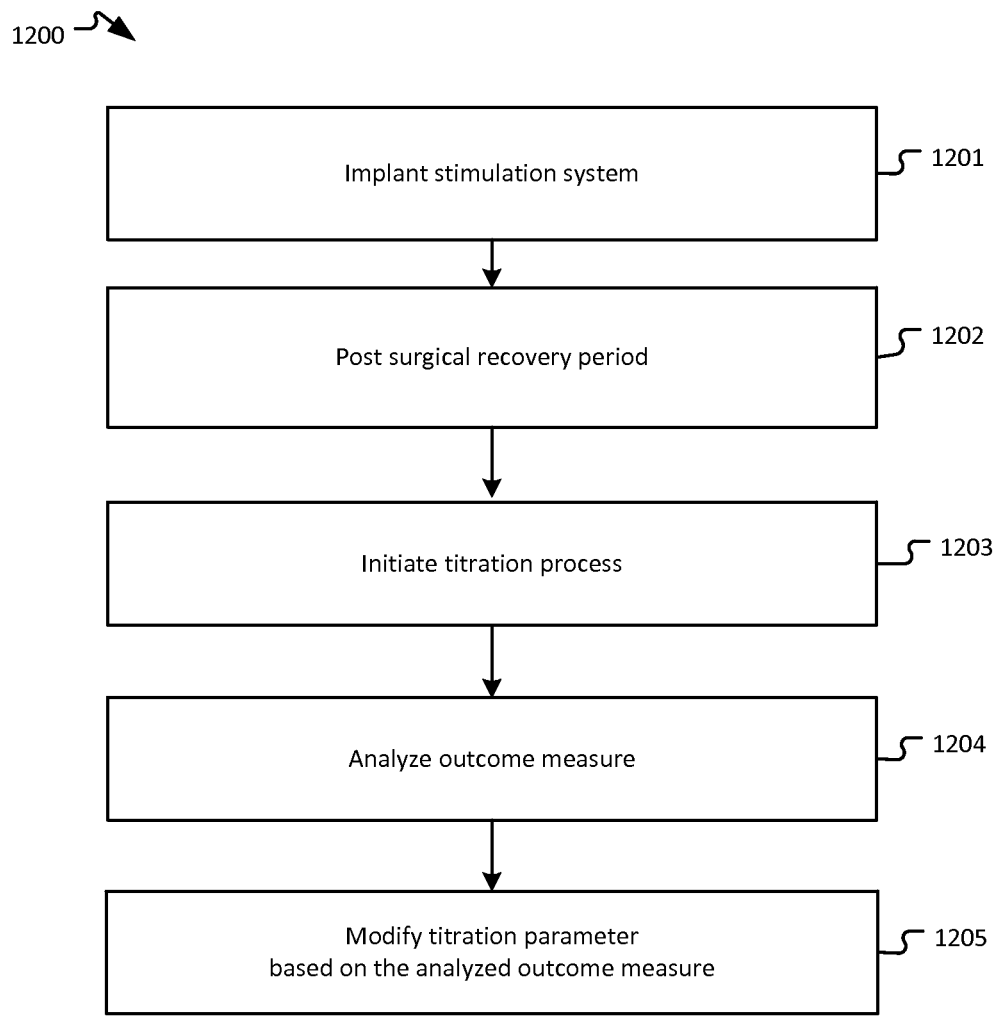
FIG. 12 illustrates a titration process with variable titration parameters in accordance with embodiments of the present invention.

In accordance with some embodiments of the present invention, an automated titration process is provided which utilizes an acclimation interval between titration sessions that may be adjusted based on the patient's response to the stimulation. FIG. 12 illustrates a titration process 1200 with a variable acclimation interval. Steps 1201-1203 are similar to steps 901-903 illustrated in FIG. 9 and described above. However, in step 1204, an outcome measure for the titration sessions is analyzed. In step 1205, the acclimation interval between subsequent titration sessions is adjusted based on the analyzed outcome measure. If the outcome measure indicates that the patient is adapting to the stimulation at a slower than expected rate, then the acclimation interval may be increased to provide the patient with additional time to recover and adapt to each set of increased stimulation intensities. Conversely, if the outcome measure indicates that the patient is adapting to the stimulation at a faster than expected rate, then the acclimation interval may be decreased to accelerate the adaption process and reduce the overall time required to complete the titration process and achieve a tolerable therapeutic maintenance dose level. Alternatively or in addition, the increments for increases in one or more stimulation parameters (e.g., current amplitude, pulse width, frequency, and OFF time) can be increased so that each titration step raises the stimulation parameter(s) by larger amounts.

Any of a variety of outcome measures may be used. In some embodiments, the outcome measure is the patient's tolerance of a targeted increase in one or more of the stimulation parameters. For example, if the patient is unable to tolerate any increase in stimulation output current (or stimulation parameter) over the course of two or more titration sessions separated by a default acclimation interval (e.g., two weeks), it may be concluded that the patient is adapting to the stimulation at a slower than expected rate. In response, the acclimation interval between subsequent titration sessions may be increased (to, e.g., three or more weeks). If the patient continues to be incapable of tolerating any increase in stimulation output current in subsequent titration sessions, then the acclimation interval may be increased again (to, e.g., four or more weeks).

In some cases, the patient may initially adapt to the increased stimulation intensity at a slower than expected rate, but after the acclimation interval is increased and subsequent titration sessions are successful at achieving the desired outcome measure, the patient's adaptation may accelerate, thereby permitting reduction of the acclimation interval back to the initial interval length. Accordingly, if the patient begins to adapt to the titration sessions after an increase in the acclimation interval, the system 1100 may be programmed to gradually reduce the acclimation interval in subsequent titration sessions.

In various embodiments described above, after a titration session is terminated, the system may be programmed to continue delivering stimulation at the last parameter settings achieved prior to conclusion of the titration session at an intensity just below the patient's tolerance zone boundary. This stimulation is delivered at this constant intensity until the next titration session is initiated. In some cases, patients are capable of enduring stimulation intensities just past the tolerance zone boundary for limited periods of time. The intensity levels just past the tolerance zone boundary may be considered by the patient as "moderately tolerable." Patients may be willing to endure stimulation at the moderately tolerable levels for limited periods of time if it results in acceleration of the adaption process.

In accordance with some embodiments, after a titration session is concluded or at any desired periodicity during the acclimation interval, an elevated stimulation session may be initiated, during which time stimulation at moderately tolerable levels exceeding the tolerance zone boundary is delivered. This elevated stimulation session may continue for any desired period of time, such as, e.g., several minutes or several hours, after which point the stimulation intensity will be reduced to a sustained stimulation intensity level below the tolerance zone boundary. In some embodiments, the elevated stimulation session may continue for less than one day, while the sustained stimulation is delivered for a period greater than one day, or the elevated stimulation session may continue for less than six hours, while the sustained stimulation is delivered for a period greater than one week. Any desired periods of time may be used.

Interactive Training Sessions

Various methods are described herein for titrating stimulation by gradually increasing stimulation intensity until the patient's tolerance zone boundary is reached or exceeded. In accordance with embodiments of the present invention, systems and methods are provided for performing interactive training sessions in clinic for patients about to undergo titration on an ambulatory basis. The methods permit clinicians to create a series of stimulation intensities (ranging from un-noticeable to noticeable but tolerable to intolerable), the patient's response to each stimulation, and the implanted device's response to patient inputs.

The implanted medical device 1100 may be used in conjunction with an external clinician programmer 1107 and patient input device (e.g., patient magnet 1130 or wireless-communications-enabled patient control device), to perform the titration processes on an ambulatory basis as described above, but is also programmed to execute in a training mode. This training mode may be initiated by the clinician using the clinician programmer 1107 while the patient is physically in the clinic for treatment and training. The training mode may be similar to the titration sessions described above, except that the increasing stimulation is initiated by the clinician using the programmer 1107 or automatically on an accelerated schedule. When the stimulation intensity reaches the patient's tolerance zone boundary, the patient can use any of the herein described methods for providing a patient input to the device 1100 to indicate that the tolerance zone boundary has been reached. When in training mode, the device 1100 may also transmit to the clinician programmer 1107 information regarding the stimulation being delivered. The programmer 1107 may include a display which permits the clinician to observe the increasing intensity and receive a report of the intensity level that elicited the patient input indicating that the tolerance zone boundary was reached. The display on the programmer 1107 may also be used to display feedback or instructions to the patient.

The clinician may run the training mode multiple times so that the patient may become proficient at recognizing stimulation levels that are noticeable but tolerable, and distinguishing those tolerable levels from the truly intolerable stimulation levels. This can also provide training for the patient in the proper use of the patient input device. In some embodiments, the programmer 1107 may be used to select the stimulation parameter to be increased (e.g., output current, frequency, pulse width, or duty cycle), so that the patient and clinician can observe the different responses that may be elicited depending on the parameter being adjusted. In some embodiments, the programmer 1107 may be configured to pause the titration algorithm to hold the stimulation at a single level. This may be useful for facilitating a tolerance zone assessment by providing the patient additional time to experience the stimulation. The programmer 1107 may also be used to terminate the training mode and return the device 1100 to its normal ambulatory mode, during which the desired ambulatory titration process may be performed.

The training mode may also comprise an algorithm that sequences stimulation changes based on the training mode parameters programmed by the clinician. Stimulation may be altered on a highly accelerated time scale in order to move the patient from tolerable to noticeable-but-tolerable to intolerable stimulation levels within the normal office follow-up period. This accelerated time scale may be, for example, five, ten or fifteen minutes for all training. This is in contrast to the ambulatory mode titration process that seeks to advance therapy levels without the patient exceeding the tolerance-zone boundary. Having the patient experience all three tolerance phases in a single clinic visit can provide valuable patient training, resulting in accelerated adaptation speed.

The system 1100 may be programmed with an autonomous monitor to ensure that the training mode terminates automatically after a certain period has elapsed, even in the absence of a termination input from the clinician programmer. For example, the system 1100 may be programmed to automatically time-out and terminate the training mode 24 hours after initiation. After this automatic time-out, the system 1100 may automatically initiate the ambulatory mode.

As a result, the system may enable patients to experience stimulation levels (usually following a stimulation increase) that may be unacceptable. Patients may also learn how to effectively deal with the intolerance through the use of the external patient input device. Clinicians can learn how individual patients react to various stimulation levels and the patients' cognitive ability to deal with unacceptable stimulation autonomously. Clinicians may also gain a sense of stimulation increases that an individual patient can tolerate and adjust the ambulatory titration algorithm accordingly.

While the invention has been particularly shown and described as referenced to the embodiments thereof, those skilled in the art will understand that the foregoing and other changes in form and detail may be made therein without departing from the spirit and scope. For example, in various embodiments described above, the stimulation is applied to the vagus nerve. Alternatively, spinal cord stimulation (SCS) may be used in place of or in addition to vagus nerve stimulation for the above-described therapies. SCS may utilize stimulating electrodes implanted in the epidural space, an electrical pulse generator implanted in the lower abdominal area or gluteal region, and conducting wires coupling the stimulating electrodes to the generator.

What is claimed is:

1. A method of operating an implantable medical device (IMD) comprising a neurostimulator coupled to an electrode assembly, said method comprising:
    initiating a plurality of titration sessions, each titration session separated from an adjacent titration session by an acclimation interval, wherein the titration sessions comprise activating the IMD to deliver a stimulation signal of gradually increasing intensity until the patient exceeds a side effect tolerance zone boundary, wherein the stimulation signal comprises a frequency in a range of 5 Hz to 10 Hz;
    analyzing an outcome measure of the plurality of titration sessions including determining whether the outcome measure indicates expected patient adaptation; and
    modifying one or more stimulation parameters based on the analyzed outcome measure relative to the expected patient adaptation.

2. The method according to claim 1, wherein modifying one or more stimulation parameters comprises modifying the acclimation interval until a subsequent titration session based on the analyzed outcome measure.

3. The method according to claim 2, wherein modifying the acclimation interval comprises at least one of:
    increasing the acclimation interval in response to the outcome measure indicating slower than expected patient adaptation,
    increasing the acclimation interval in response to the outcome measure indicating a failure to achieve a target increase in stimulation intensity, increasing the acclimation interval in response to the outcome measure indicating a failure to achieve a target increase in output current over the plurality of titration sessions, wherein the stimulation signal comprises the output current, or decreasing the acclimation interval before the subsequent titration session in response to the outcome measure indicating faster than expected patient adaptation.

4. The method according to claim 2, further comprising, during the acclimation intervals, activating the IMD to deliver the stimulation signal at an intensity resulting in an acceptable side effect level.

5. The method according to claim 1, further comprising:
determining a maintenance dosage level corresponding to a tolerable stimulation intensity achieving adequate adaptation; and
delivering stimulation at the maintenance dosage level.

6. The method according to claim 1, further comprising receiving a patient input indicating the side effect tolerance zone boundary by at least one of:
receiving a radio frequency (RF) signal from an external communications device, said RF signal indicating that the patient has reached the side effect tolerance zone boundary,
detecting a magnetic field indicating that the patient has reached the side effect tolerance zone boundary,
detecting an acoustic signal indicating that the patient has reached the side effect tolerance zone boundary, or
detecting a motion signal with a motion sensor indicating that the patient has reached the side effect tolerance zone boundary.

7. The method according to claim 1, further comprising:
initiating an elevated stimulation session at an elevated stimulation intensity for a first period of time; and
after the first period of time, initiating sustained stimulation at a sustained stimulation intensity for a second period of time, wherein the elevated stimulation intensity is greater than the sustained stimulation intensity.

8. A method of operating an implantable medical device (IMD) comprising a neurostimulator coupled to an electrode assembly, said method comprising:
initiating a plurality of titration sessions, each titration session separated from an adjacent titration session by an acclimation interval, wherein the titration sessions comprise activating the IMD to deliver a stimulation signal of gradually increasing intensity until the patient exceeds a side effect tolerance zone boundary, wherein the stimulation signal comprises a frequency in a range of 5 Hz to 10 Hz;
analyzing an outcome measure of the plurality of titration sessions; and
modifying one or more stimulation parameters based on the analyzed outcome measure.

9. The method according to claim 8, further comprising:
delivering the frequency of the stimulation signal at 10 Hz; and
upon the patient exceeding the side effect tolerance zone boundary, decreasing the frequency to 5 Hz.

10. The method according to claim 8, wherein modifying one or more stimulation parameters comprises modifying the acclimation interval until a subsequent titration session based on the analyzed outcome measure.

11. The method according to claim 10, wherein modifying the acclimation interval comprises at least one of:
increasing the acclimation interval in response to the outcome measure indicating slower than expected patient adaptation,
increasing the acclimation interval in response to the outcome measure indicating a failure to achieve a target increase in stimulation intensity,
increasing the acclimation interval in response to the outcome measure indicating a failure to achieve a target increase in output current over the plurality of titration sessions, wherein the stimulation signal comprises the output current, or
decreasing the acclimation interval before the subsequent titration session in response to the outcome measure indicating faster than expected patient adaptation.

12. The method according to claim 10, further comprising, during the acclimation intervals, activating the IMD to deliver the stimulation signal at an intensity resulting in an acceptable side effect level.

13. The method according to claim 8, further comprising:
determining a maintenance dosage level corresponding to a tolerable stimulation intensity achieving adequate adaptation; and
delivering stimulation at the maintenance dosage level.

14. The method according to claim 8, further comprising receiving a patient input indicating the side effect tolerance zone boundary by at least one of:
receiving a radio frequency (RF) signal from an external communications device, said RF signal indicating that the patient has reached the side effect tolerance zone boundary,
detecting a magnetic field indicating that the patient has reached the side effect tolerance zone boundary,
detecting an acoustic signal indicating that the patient has reached the side effect tolerance zone boundary, or
detecting a motion signal with a motion sensor indicating that the patient has reached the side effect tolerance zone boundary.

15. The method according to claim 8, further comprising:
initiating an elevated stimulation session at an elevated stimulation intensity for a first period of time; and
after the first period of time, initiating sustained stimulation at a sustained stimulation intensity for a second period of time, wherein the elevated stimulation intensity is greater than the sustained stimulation intensity.

16. An implantable medical device comprising:
an electrode assembly;
a neurostimulator coupled to the electrode assembly, the neurostimulator configured to:
initiate a plurality of titration sessions, each titration session separated from an adjacent titration session by an acclimation interval, wherein the titration sessions comprise activating the implantable medical device to deliver a stimulation signal of gradually increasing intensity until the patient exceeds a side effect tolerance zone boundary, wherein the stimulation signal comprises a frequency in a range of 5 Hz to 10 Hz;
analyze an outcome measure of the plurality of titration sessions; and
modify one or more stimulation parameters based on the analyzed outcome measure.

17. The implantable medical device according to claim 16, wherein the neurostimulator is configured to:
deliver the frequency of the stimulation signal at 10 Hz; and
upon the patient exceeding the side effect tolerance zone boundary, decrease the frequency to 5 Hz.

18. The implantable medical device according to claim 16, wherein the neurostimulator is configured to modify the acclimation interval until a subsequent titration session based on the analyzed outcome measure.

19. The implantable medical device according to claim 18, wherein the neurostimulator is configured to modify the acclimation interval by at least one of:
- increasing the acclimation interval in response to the outcome measure indicating slower than expected patient adaptation,
- increasing the acclimation interval in response to the outcome measure indicating a failure to achieve a target increase in stimulation intensity,
- increasing the acclimation interval in response to the outcome measure indicating a failure to achieve a target increase in output current over the plurality of titration sessions, wherein the stimulation signal comprises the output current, or
- decreasing the acclimation interval before the subsequent titration session in response to the outcome measure indicating faster than expected patient adaptation.

20. The implantable medical device according to claim 16, wherein the neurostimulator is configured to receive a patient input indicating the side effect tolerance zone boundary by at least one of:
- receiving a radio frequency (RF) signal from an external communications device, said RF signal indicating that the patient has reached the side effect tolerance zone boundary,
- detecting a magnetic field indicating that the patient has reached the side effect tolerance zone boundary,
- detecting an acoustic signal indicating that the patient has reached the side effect tolerance zone boundary, or
- detecting a motion signal with a motion sensor indicating that the patient has reached the side effect tolerance zone boundary.

* * * * *